US007501496B1

(12) United States Patent
Endl et al.

(10) Patent No.: US 7,501,496 B1
(45) Date of Patent: Mar. 10, 2009

(54) ANTI-OX40L ANTIBODIES

(75) Inventors: Joseph Endl, Wilhelm (DE); Elsie M. Eugui, Belmont, CA (US); Maria Elena Fuentes, Sunnyvale, CA (US); Yvo Graus, Odijk (NL); Aran Frank Labrijn, Amsterdam (NL); Martin Lanzendoerfer, Tutzing (DE); Paul Parren, Odijk (NL); Frank Rebers, Utrecht (NL); Ralf Schumacher, Penzberg (DE); Stefan Seeber, Penzberg (DE); Jan Van De Winkel, Zeist (NL); Martine Van Vugt, Houten (NL)

(73) Assignee: Roche Palo Alto LLC, Palo Alto, CA (US)

( * ) Notice: Subject to any disclaimer, the term of this patent is extended or adjusted under 35 U.S.C. 154(b) by 54 days.

(21) Appl. No.: 11/229,162

(22) Filed: Sep. 16, 2005

(30) Foreign Application Priority Data

Sep. 17, 2004 (EP) .................................. 04022158
Dec. 23, 2004 (EP) .................................. 04030546

(51) Int. Cl.
*C07K 16/00* (2006.01)
*C07K 16/28* (2006.01)
*A61K 39/395* (2006.01)

(52) U.S. Cl. ............. 530/387.3; 530/388.1; 530/388.22; 530/388.7; 424/133.1; 424/141.1; 424/152.1; 424/153.1

(58) Field of Classification Search ...................... None
See application file for complete search history.

(56) References Cited

U.S. PATENT DOCUMENTS

| 4,179,337 | A | 12/1979 | Davis et al. | |
|---|---|---|---|---|
| 4,301,144 | A | 11/1981 | Iwashita et al. | |
| 4,496,689 | A | 1/1985 | Mitra | |
| 4,640,835 | A | 2/1987 | Shimizu et al. | |
| 4,670,417 | A | 6/1987 | Iwasaki et al. | |
| 4,791,192 | A | 12/1988 | Nakagawa et al. | |
| 5,202,238 | A | 4/1993 | Fell, Jr. et al. | |
| 5,204,244 | A | 4/1993 | Fell et al. | |
| 5,545,806 | A | 8/1996 | Lonberg et al. | |
| 5,545,807 | A | 8/1996 | Surani et al. | |
| 5,569,825 | A | 10/1996 | Lonberg et al. | |
| 5,625,126 | A | 4/1997 | Lonberg et al. | |
| 5,633,425 | A | 5/1997 | Lonberg et al. | |
| 5,661,016 | A | 8/1997 | Lonberg et al. | |
| 5,770,429 | A | 6/1998 | Lonberg et al. | |
| 5,789,650 | A | 8/1998 | Lonberg et al. | |
| 5,814,318 | A | 9/1998 | Lonberg et al. | |
| 5,874,299 | A | 2/1999 | Lonberg et al. | |
| 5,877,397 | A | 3/1999 | Lonberg et al. | |
| 6,632,927 | B2* | 10/2003 | Adair et al. | ............... 530/387.3 |
| 6,936,698 | B2* | 8/2005 | Taylor | ..................... 530/387.3 |
| 2006/0235208 | A1* | 10/2006 | Lazar et al. | ............ 530/388.22 |

FOREIGN PATENT DOCUMENTS

| EP | 0 307 434 B1 | 9/1993 |
|---|---|---|
| WO | WO 87/0533 A1 | 11/1987 |
| WO | WO 92/03918 A1 | 3/1992 |
| WO | WO 92/12227 A1 | 7/1992 |
| WO | WO 92/22645 A1 | 12/1992 |
| WO | WO 94/11026 A1 | 5/1994 |
| WO | WO 94/25585 A2 | 11/1994 |
| WO | WO 95/05468 A | 2/1995 |
| WO | WO 95/12673 A1 | 5/1995 |
| WO | WO 95/21915 A1 | 8/1995 |
| WO | WO 98/24884 A1 | 6/1998 |
| WO | WO 99/15200 A1 | 4/1999 |
| WO | WO 99/58572 A | 11/1999 |
| WO | WO 01/14424 A2 | 3/2001 |
| WO | WO 01/25492 A1 | 4/2001 |
| WO | WO 01/94586 A2 | 12/2001 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Hezareh, M., et al., *Effector function activities of a panel of mutants of a broadly neutralizing antibody against human immunodeficiency virus type 1*, Journal of Virology, 2001, pp. 12161-12168, vol. 75(24).
Nohara. C., et al., *Amelioration of experimental autoimmune encephalomyelitis with anti-OX40 ligand monoclonal antibody: a critical role for OX40 ligand in migration, but not development, of pathogenic T cells*, Journal of Immunology, 2001, pp. 2108-2115, vol. 166(3).
Wang. Q., et al., *Characterization and functional study of five novel monoclonal antibodies against human OX40L highlight reverse signaling: enhancement of IgG production of B cells and promotion of maturation of DCs*, Tissue Antigens, 2004, pp. 566-574, vol. 64(5).
Akiba, H., et al., "CD28-Independent Costimulation of T Cells by OX40 Ligand and CD70 on Activated B Cells," *J Immunol*. Jun. 15, 1999; 162(12):7058-66.
Arestides, R.S., et al., "Costimulatory Molecule OX40L is Critical for Both Th1 and Th2 Responses in Allergic Inflammation," *Eur. J. Immunol*. Oct. 2002; 32(10):2874-80.
Bertram, E.M., et al., "Role of T Cell Costimulation in Anti-Viral Immunity," *Semin Immunol*. Jun. 2004; 16(3):185-96. Review.
Burgess, J.K., et. al., "Detection and Characterization of OX40 Ligand Expression in Human Airway Smooth Mucsle Cells: A Possible Role in Asthma?," *J Allergy Clin Immunol*. Apr. 2004 113(4):683-9.
Chen, A.I., et al.; "Ox40-Ligand Has a Critical Costimulatory Role in Dendritic Cell: T Cell Interactions," *Immunity*. Dec. 1999; 11(6):689-98.
Gramaglia, I., et al., "The OX40 Costimulatory Receptor Determines the Development of CD4 Memory by Regulating Primary Clonal Expansion," *J Immunol*. Sep. 15, 2000; 165(6):3043-50.
Grosenbach, D.W., et al., "A Recombinant Vector Expressing (Continued)

*Primary Examiner*—Ilia Ouspenski
(74) *Attorney, Agent, or Firm*—Grant D. Green

(57) ABSTRACT

This invention relates to anti-OX40L antibodies and, in particular, to anti-OX40L antibodies and variants thereof that contain a Fc part derived from human origin and do not bind complement factor C1q. These antibodies have new and inventive properties causing a benefit for a patient suffering from inflammatory diseases.

26 Claims, 10 Drawing Sheets

OTHER PUBLICATIONS

Transgenes for Four T-Cell Costimulatory Molecules (OX40L, B7-1, ICAM-1, LFA-3) Induces Sustained CD4+ and CD8+ T-Cell Activation, Protection from Apoptosis, and Enhanced Cytokine Production," Cell *Immunol.* Mar. 2003; 222(1):45-57.

Gruss, H.J. "Molecular, Structure, and Biological Characteristics of the Tumor Necrosis Factor Ligand Superfamily," Int. J. Clin. Lab Res 1996; 26(3): 143-59.

Hoshino, A., et al., "Crtitical Role for OX40 Ligand in the Development of Pathogenic Th2 Cells in a Murine Model of Asthma," *Eur J Immunol*. Apr. 2003; 33(4):861-9.

Ishii, et al., "OX40 (CD134) and OX40 Ligand Interaction Plays an Adjuvant Role during In Vivo Th2 Responses," Eur J Immunol. Sep. 2003; 33(9)2372-81.

Ito, T., et al., "Plasmacytoid Dentritic Cells Regulate Th Cell Responses through OX40 Ligand and Type I IFNs[1]," *J Immunol*. Apr. 1, 2004; 172(7):4253-9.

Kato, H., et al., Essential Role of OX40L on B Cells in Persistent Alloantibody Production Following Repeated Alloimmunizations, *J Clin Immunol.* May 2004; 24(3):237-48.

Linton, P.J., et al., "Costimulation via OX40L Expressed by B Cells Sufficient to Determine the Extent of Primary CD4 Cell Expansion and Th2 Cytokine Secretion In Vivo," *J. Exp Med.* Apr. 7, 2003; 197(7):875-83. Epub Mar. 31, 2003.

Murata, K., et al., "Constitutive OX40/OX40 Ligand Interaction Induces Autoimmune-Like Diseases," *J. Immunol.* Oct. 15, 2002; 169(8):4628-36.

Murata, K., et al., "Impairment of Antigen-Presenting Cell Function in Mice Lacking Expression of OX40 Ligand," *J. Exp Med.* Jan. 17, 2000; 191(2):365-74.

Ndhlovu, L.C., et al., "Critical Involvement of OX40 Ligand Signals in the T Cell Priming Events During Experimental Autoimmune Encephalomyelitis," *J Immunol.* Sep. 1, 2001; 167(5):2991-9.

Nohara, C., et al., "Amelioration of Experimental Autoimmune Encephalomyelitis with Anti-OX40 Ligand Monoclonal Antibody: A Critical Role for OX40 Ligand in Migration, But Not Development, of Pathogenic T Cells," *J Immunol*. Feb. 1, 2001; 166(3):2108-15.

Obermeier, F., et al., "OX40/OX40L Interaction Induces the Expression of CXCR5 and Contributes to Chronic Colitis induced by Dextran Sulfate Sodium in Mice," *Eur J Immunol.* Dec. 2003; 33(12):3265-74.

Ohshima, Y., et al., "Expression and Function of OX40 Ligand on Human Dendritic Cells," *J. Immunol.* Oct. 15, 1997; 159(8):3838-48.

Salek-Ardakani, S., et al., "OX40 (CD134) Controls Memory T Helper 2 Cells that Drive Lung Inflammation," *J Exp Med.* Jul. 21, 2003; 198(2):315-24. Epub Jul. 14, 2003.

Sato, T., et al., "Consequences of OX40-OX40 Ligand Interactions in Langerhans Cell Funtion: Enhanced Contact Hypersensitivity Responses in OX40L-Transgenic Mice," *Eur J Immunol*. Nov. 2002; 32(11):3326-35.

Straw, A.D., et al., "CD154 Plays a Central Role in Regulating Dendritic Cell Activation During Infections That Induce Th1 and Th2 Responses," *J. Immunol.* Jan. 15, 2003; 170(2):727-34.

Stuber, E., et al., "The Expression of OX40 in Immunologically Mediated Diseases of the Gastrointestinal Tract (Celiac Disease, Crohn's Disease, Ulcerative Colitis)," *Eur J Clin Invest*. Jul. 2000; 30(7):594-9.

Stuber, E., et al., "The T Cell-B Cell Interaction via OX40-OX40L is Necessary for the T Cell-Dependent Humoral Immune Response," *J. Exp. Med.* Mar. 1, 1996; 183(3):979-89.

Takeda, I., et al., "Distinct Roles for the OX40-OX40 Ligand Interaction in Regulatory and Nonregulatory T Cells," *J Immunol.* Mar. 15, 2004; 172(6):3580-9.

Totsuka, T., et al., "Therapeutic Effect of Anti-OX40L and Anti-TNF-alpha MAbs in a Murine Model of Chronic Colitis," *Am J Physiol Gastrointest Liver Physiol*. Apr. 2003; 284(4):G595-603. Epub Jan. 10, 2003.

Ukyo, N., et al., Costimulation through OX40 is Crucial for Induction of an Alloreactive Human T-Cell Response, *Immunology*. Jun. 2003; 109(2):226-31.

Yoshioka, T., et al., "Contribution of OX40/OX40 Ligand Interation to the Pathogenesis of Rheumatoid Arthritis," *Eur J Immunol*. Oct. 2000; 30(10):2815-23.

Gram, H. et al., "In Vitro Selection and Affinity Maturation of Antibodies from a Naïve Combinatorial Immunoglobulin Library," *Proc. Natl. Acad. Sci. USA* 89 (1992) 3576-3580.

Satake, Y. et al., "Characterization of Rat OX40 Ligand by Monoclonal Antibody," *Biochemical and Biophysical Research Communications* 270 (2000) 1041-1048.

Akiba, H. et al., "Identification of Rat OX40 Ligand by Molecular Cloning," *Biochem. Biophys. Res. Commun.* 251 (1998) 131-136.

Akiba, H. et al., "Critical Contribution of OX40 Ligand to T Helper Cell Type 2 Differentiation in Experimental Leishmaniasis," *J. Exp. Med.* 191 (2000) 375-380.

Angal, S. et al., "A Single Amino Acid Substitution Abolishes the Heterogeneity of Chimeric Mouse/Human (IgG4) Antibody," *Mol. Immunol.* 30 (1993) 105-108.

Aplin J.D., et al., "Preparation, Properties, and Applications of Carbohydrate Conjugates of Proteins and Lipids," *CRC Crit. Rev. Biochem.* 10 (1981) 259-306.

Armour, K.L., et al., "Recombinant human IgG Molecules lacking Fcγ receptor I binding and monocyte triggering activities," *Eur. J. Immunol.* 29 (1999) 2613-2624.

Ausubel, F., et al., "Current Protocols in Molecular Biology," *ed., Current Protocols in Molecular Biology*, Greene Publishing and Wiley Interscience, New York (1987).

Barnes, L.M., et al., "Characterization of the Stability of Recombinant Protein Production in the GS-NS0 Expression System," Biotech. Bioeng. 73 (2001) 261-270.

Barnes, L.M., et al., "Advances in animal cell recombinant protein production: GS-NS0 expression system," Cytotechnology 32 (2000) 109-123.

Baum, P.R., et al., Molecular Characterization of Murine and Human OX40/OX40 Ligand Systems: Indentification of a human OX40 ligand as the HTLV-1-regulated protein, EMBO J. 13 (1994) 3992-4001.

Blazer, B.R., et al., "Ligation of OX40 (CD134) regulates graft-versus-host disease (GVHD) and graft rejection in allogeneic bone marrow transplant recipients," *Blood* 101 (2003) 3741-3748.

Boerner, P., et al., Production of Antigen-specific human monoclonal antibodies from in vitro-primed human splenosytes, *J. Immunol.* 147 (1991) 86-95.

Brüggermann, M., et al., "Designer Mice: The Production of Human Antibody Repertoires in Transgenic Animals," *Year Immunol.* 7 (1993) 33-40.

Brunhouse, R., et al., "Isotypes of IgG: Comparison of the Primary Structures of Three Pairs of Isotypes which Differ in their ability to activate complement," *Mol. Immunol.* 16 (1979) 907-917.

Burton, D.R. et al., "The C1q Receptor Site on Immunoglobulin G," *Nature* 288 (1980) 338-344.

Burton, D.R. et al., "Immunoglobulin G: Functional Sites," *Mol. Immunol.* 22 (1985) 161-206.

Capel, J.A., et al., "Hetergeneity of Human IgG Fc Receptors," *Immunomethods* 4 (1994) 25-31.

Carter, P., et al., "Humanization of an Anti-p185 [HER2] antibody for human Cancer Therapy," *Proc. Natl. Acad. Sci. USA* 89 (1992) 4285-4289.

Chen, J., et al., "B Cell Development in Mice that Lack One or Both Immunoglobulin K light chain genes," *EMBO J*. 12 (1993) 821-830.

Chen, J., et al.,Immunoglobulin Gene Rearrangement in B Cell Deficient Mice Generated by Targeted Deletion of the $J_H$ locus, *Int. Immunol.* 5 (1993) 647-656.

Choi, T.K., et al., "Transgenic Mice Containing a Human heavy chain immunoglobulin gene fragment cloned in a yeast artificial chromosome," *Nature Genetics* 4 (1993) 117-123.

Cole, S.B.C., et al., The EBV-Hybridoma Technique and its application to Human Lung Cancer, *Monoclonal Antibodies and Cancer Therapy*, Alan R. Liss (1985) 77-96.

De Haas, M., et al., "Fcγ Receptors of Phagocytes," *J. Lab. Clin. Med.* 126 (1995) 330-341.

Duncan, A.R., et al., "The Binding Site for C1q on IgG," *Nature* 332 (1988) 738-740.

Durocher, Y., et al., "High-level and high-throughout Recombinant Protein Production by Transient Transfection of Suspension-growing Human 293-EBNA1 Cells," *Nucl. Acids Res.* 30 (2002) E9.

Edelman, G.M., et al., The Convalent Structure of an Entire γG Immunoglobulin Molecule, *Proc. Natl. Acad. Sci. USA* 63 (1969) 78-85.

Edge, A.S., et al., "Deglycosylation of Glycoproteins by Trifluoromethanesulfonic Acid," *Anal. Biochem.* 118 (1981) 131-137.

Fishwild, D.M., et al., "High-avidity human IgGκ Monoclonal Antibodies from a Novel Strain of Minilocus Transgenic Mice," *Nat. Biotechnol.* 14 (1996) 845-851.

Geisse, S. et al., "Eukaryotic Expression Systems: A Comparison," *Protein Expr. Purif.* 8 (1996) 271-282.

Gessner, J.E., et al., "The IgG Fc Receptor Family," *Ann. Hematol.* 76 (1998) 231-248.

Harding, F., et al., "Class Switching in Human Immunoglobulin Transgenic Mice," *Ann. N. Y. Acad. Sci.* 764 (1995) 536-546.

Higgins, L.M., et al., "Regulation of T Cell Activation In Vitro and In Vivo by Targeting the OX40-OX40 Ligand Interaction: Amelioration of Ongoing Inflammatory Bowel Disease with an OX40-IgG Fusion Protein, But Not with an OX40 Ligand-IgG Fusion Protein," *J. Immunol.* 162 (1999) 486-493.

Hoogenboom H.R., et al., "By-passing Immunisation Human Antibodies from Synthetic Repertoires of Germline $V_H$ Gene Segments Rearranged in Vitro," *J. Mol. Biol.* 227 (1992) 381-388.

Humphreys, I.R., et al., "A Critical Role for OX40 in T Cell-mediated Immunopathology during Lung Viral Infection," *J. Exp. Med.* 198 (2003) 1237-1242.

Idusogie, E.E., et al., "Mapping of the C1q Binding Site on Rituxan, a Chimeric Antibody with a Human IgG1 Fc," *J. Immunol.* 164 (2000) 4178-4184.

Imura, A. et al., "OX40 Expressed on Fresh Leukemic Cells from Adult T-Cell Leukemia Patients Mediates Cell Adhesion to Vascular Endothelial Cells: Implication for the Possible Involvement of OX40 in Leukemic Cell Infiltration," *Blood* 89 (1997) 2951-2958.

Imura, A. et al., "The Human OX40/gp34 System Directly Mediates Adhesion of Activate T Cells to Vascular Endothelial Cells," *J. Exp. Med.* 183 (1996) 2185-2195.

Jakobovits, A., et al., "Germ-line transmission and Expression of a Human-derived yeast Artifical Chromosome," *Nature* 362 (1993) 255-258.

Jakobovits, A., et al., "Analysis of Homozygous Mutant Chimeric Mice: Deletion of the Immunoglobulin Heavy-chain joining Region blocks B-cell development and Antibody Production," *Proc. Natl. Acad. Sci. USA* 90 (1993) 2551-2555.

Jones, B., et al., "Different Phenotypic variants of the Mouse B Cell Tumor A20/2J are selected by Antigen- and Mitogen-Triggered Cytotoxicity of L3T4-Positive, I-A-Restricted T Cell Clones[1]," *J. Immunol.* 136 (1986) 348-356.

Jones, P., et al., "Replacing the Complementarity-determining Regions in a Human Antibody with those from a mouse," *Nature* 321 (1986) 522-525.

Kabat, E.A., et al., "Sequences of Proteins of Immunogical Interest," 5th Ed., Public Health Service, National Institutes of Health, Bethesda, MD (1991).

Kaufman R.J., "Overview of Vector Design for Mammalian Gene Expression," *Molecular Biotechnology* 16 (2000) 151-161.

Kjaergaard J., et al., "Augmentation Versus Inhibition: Effects of Conjunctional OX40 Receptor Monoclonal Antibody and IL-2 Treatment on Adoptive Immunotherapy of Advanced Tumor[1]," *J. Immunol.* 167 (2001) 6669-6677.

Kotani, A., et al., "Signaling of gp34 (OX40 ligand) induces vascular endothelial cells to produce a CC Chemokine RANTES/CCL5," *Immunol. Letters* 84 (2002) 1-7.

Lane, P., "Role of OX40 Signals in Coordinating CD4 T Cell Selection, Migration, and Cytokine Differentiation in T Helper (Th) 1 and Th2 Cells," *J. Exp. Med.* 191 (2000) 201-206.

Lonberg, N., et al., "Human Antibodies from Transgenic Mice," *Intern. Rev. Immunol.* 25 (1995) 65-93.

Lonberg, N., et al., "Antigen-specific human antibodies from mice comprising four distinct genetic modifications," *Nature* 368 (1994) 856-859.

Lonberg, N., "Transgenic Approaches to Human Monoclonal Antibodies," *Handbook of Experimental Pharmacology* 113 (1994) 49-101.

Lukas, T.J., et al., "Inhibition of C1-Mediated Immune Hemolysis by Monomeric and Dimeric Peptides from the Second Constant Domain of Human Immunoglobulin G[1]," *J. Immunol.* 127 (1981) 2555-2560.

Lund, J., et al., "Oligosaccharide-protein interactions in IgG can modulate recognition by Fcγ Receptor," *FASEB J.* (1995) 115-119.

Makrides, S.C., et al., "Components of Vectors for Gene Transfer and Expression in Mammalian Cells," *Protein Expression and Purif.* 17 (1999) 183-202.

Mallett, S., et al., "A New Superfamily of Cell Surface Proteins related to the Nerve Growth Factor Receptor," *Immunol. Today* 12 (1991) 220-223.

Mallett, S., et al., "Characterization of the MRC OX40 Antigen of Activated CD4 Positive T Lymphocytes—a molecule related to nerve factor receptor," *EMBO J.* 9 (1990) 1063-1068.

Marks, J.D., et al., "Human Antibodies from V-gene Libraries Displayed on Phage," *J. Mol. Biol.* 222 (1999) 581-597.

Matsumura, Y., et al., "Intracellular Signaling of gp34, the OX40 Ligand: Induction of c-jun and c-fos m-RNA Expression Through gp34 upon Binding of Its Receptor, $OX40^1$," *J. Immunol.* 163 (1999) 3007-3011.

Meissner, P., et al., "Transient Gene Expression: Recombinant Protein Production with Suspension-Adapted HEK293=EBNA Cells," *Biotechnol. Bioeng.* 75 (2001) 197-203.

Miura, S., et al., "Molecular Cloning and Characterization of a Novel Glycoprotein, gp34, That is Specifically Induced by the Human T-cell Leukemia Virus Type I Transactivator $p40^{tax}$," *Molecular and Cellular Biology* 11 (1991) 1313-1325.

Morgan, A., et al., "The N-terminal end of the $C_H2$ domain of Chimeric Human IgG1 Anti-HLA-DR is Neccessory for C1q, FcγRI and FcγRIII Binding," *Immunology* 86 (1995) 319-324.

Morrison, S.L., et al. "Chimeric Human Antibody Molecules: Mouse Antigen-binding Domains with Human Constant Region Domains," *Proc. Natl. Acad. Sci. USA* 81 (1984) 6851-6855.

Neuberger, M.S., et al., "Expression and Regulation of Immunoglobulin Heavy Chain Gene Transfected into Lymphoid Cells," *EMBO J.* 2 (1983) 1373-1378.

Neuberger, M.S., et al., "A Hapten-specific Chimaeric IgE Antibody with Human Physiological effector Function," *Nature* 314 (1985) 268-270.

Norderhaug, L., et al., "Versatile vectors for transient and stable expression of recombinant antibody molecules in mammalian cells," *J. Immunol. Methods* 204 (1997) 77-87.

Orlandi, R., et al., "Cloning Immunoglobulin Variable Domains for Expression by the Polymerase Chain Reaction," *Proc. Natl. Acad. Sci. USA* 86 (1989) 3833-3837.

Picard, D., et al., "A Lymphocyte-specific Enhancer in the Mouse Immunoglobulin κ Gene," *Nature* 307 (1984) 80-82.

Queen, C., et al., "A Humanized Antibody that binds to the Interleukin 2 Receptor," *Proc. Natl. Acad. Sci. USA* 86 (1989) 10029-10033.

Ravetch, J.V., et al., "IgG Fc Receptors," *Annu. Rev. Immunol.* 19 (2001) 275-290.

Ravetch, J.V., et al., "Fc Receptors," *Annu. Rev. Immunol.* 9 (1991) 457-492.

Riechmann, L., et al., "Reshaping Human Antibodies for Therapy," *Nature* 332 (1988) 323-327.

Rogers, P.R., et al., "OX40 Promotes Bcl-xL and Bcl-2 Expression and Is Essential for Long-Term Survival of CD4 T Cells," *Immunity* 15 (2001) 445-455.

Schlaeger, E.-J., et al., "Transient Gene Expression in Mammalian Cells Grown in Serum-free Suspension Culture," *Cytotechnology* 30 (1999) 71-83.

Schlaeger, E.-J., et al., "The Protein Hydrolysate, Primatone RL, is a Cost-effective Multiple Growth Promoter of Mammalian Cells Culture in Serum-containing and Serum-free Media and displays Anti-apoptosis Properties," *J. Immunol. Methods* 194 (1996) 191-199.

Shields, R.L., et al., "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276 (2001) 6591-6604.

Sojar, H. T., et al., "A Chemical Method for the Deglycosylation of Proteins[1]," *Arch. Biochem. Biophys.* 259 (1987) 52-57.

Stüber, E., et al., "Involvement of OX40-OX40L Interactions in the Intestinal Manifestations of the Murine Acute Graft-Versus-Host Disease," *Gastroenterology* 115 (1998) 1205-1215.

Sugamura, K., et al., "Therapeutic Targeting of the Effector T-Cell Co-Stimulatory Molecule OX40," *Nat. Rev. Immunol.* 4 (2004) 420-431.

Takahashi, T., et al., "OX40 Stimulation by gp34/OX40 Ligand Enhances Productive Human Immunodeficiency Virus Type 1 Infection," *J. Virology* 75 (2001) 6748-6757.

Takasawa, N., et al., "Expression of gp34 (OX40 Ligand) and OX40 on Human T Cell Clones," *Jpn. J. Cancer Res.* 92 (2001) 377-382.

Tanaka, Y., et al., "Glycoprotein Antigen detected with new Monoclonal Antibodies on the surface of Human Lymphocytes infected with Human T-cell Leukemia virus Type-I (HTLV-I)," *Int. J. Cancer* 36 (1985) 549-555.

Taylor, L., et al., "Indentification of a Soluble OX40 isoform: Development of a Specific and Quantitative Immunoassay," *J. Immunol. Methods* 255 (2001) 67-72.

Taylor, L., et al., "Human Immunoglobulin Transgenes undergo rearrangement, somatic mutation and class switching in mice that lack endogenous IgM," *Int. Immunol.* 6 (1994) 579-591.

Taylor, L., et al., "A Transgenic Mouse that Expresses a Diversity of Human Sequence Heavy and Light Chain Immunoglobulins," *Nucleic Acids Res.* 20 (1992) 6287-6295.

Thommesen, J.E., et al., "Lysine 322 in the Human IgG3 $C_H2$ Domain is Crucial for Antibody Dependent Complement Activation," *Mol. Immunology* 37 (2000) 995-1004.

Thotakura, N.R. et al., "Enzamatic Deglycosylation of Glycoproteins," *Meth. Enzymol.* 138 (1987) 350-359.

Tozawa, H., et al., "Species-dependent Antigenicity of the 34-kDA Glycoprotein found on the membrane of various primate lymphocytes transformed by Human T-Cell Leukemia virus Type-I (HTLV-I) and Simian T-Cell Leukemia Virus (STLV-I)," *Int. J. Cancer* 41 (1988) 231-238.

Tsukada, N., et al., "Blockade of CD134 (OX40)—CD134L interaction ameliorates lethal acute graft-versus-host disease in a murine model of allogeneic bone marrow transplantation," *Blood* 95 (2000) 2434-2439.

Tuaillon, N., et al., "Biased Utilization of $D_{HQ52}$ and $J_H4$ Gene Segments in a Human Ig Transgenic Minilocus is Independent of Antigenic Selection," *J. Immunology* 152 (1994) 2912-2920.

Tuaillon, N., et al., "Human immunoglobulin heavy-chain minilocus recombination in transgenic mice: Gene-segment use in μ and γ transcripts," *Proc. Natl. Acad. Sci. USA* 90 (1993) 3720-3724.

Van De Winkel, J.G., et al., "Biology of Human Immunoglobulin G Fc Receptors," *Journal of Leukocyte Biology* 49 (1991) 511-524.

Van Dijk, M.A., et al., "Human Antibodies as Next Generation Therapeutics," *Curr. Opin. Chem. Biol.* 5 (2000) 368-374.

Vitetta, E.S., et al., "Redesigning Nature's Poisons to Create Anti-Tumor Reagents," *Science* 238 (1987) 1098-1104.

Ward, E.S., et al., "The Effector Functions of Immunoglobulins: Implications for Therapy," *Therapeutic Immunology* 2 (1995) 77-94.

Weinberg, A.D., et al., "Blocking OX-40/OX-40 Ligand Interaction In Vitro and In Vivo Leads to Decreased T Cell Function and Amerlioration of Experimental Allergic Encephalomyelitis," *J. Immunology* 162 (1999) 1818-1826.

Weinberg, A.D., et al., "Selective depletion of myelin-reactive T cells with the Anti-OX-40 antibody ameliorates autoimmune encephalomyelitis," *Nature Medicine* 2 (1996) 183-189.

Weinberg, A.D., et al., "OX-40 Life Beyond the Effector T Cell Stage," *Semin. Immunol.* 10 (1998) 471-480.

Weinberg, A.D., et al., "OX40: Targeted Immunotherapy implications for Tempering Autoimmunity and Enhancing Vaccines," *Trends Immunol.* 23 (2002) 102-109.

Werner, R.G., et al., "Appropriate Mammalian Expression Systems for Biopharmaceuticals," *Arzneimittelforschung* 48 (1998) 870-880.

Wu, T., et al., "The Effect of OX40/OX40L and CD27/CD70 Pathways on Allogeneic Islet Graft Rejection," *Transplantation Proceedings.* 33 (2001) 217-218.

Xiaoyan, Z., et al., "Expression of OX40 (CD134) on CD4+ T-cells from Patients with Myasthenia Gravis," *Clinical and Experimental Immunology* 143 (2005) 110-116.

\* cited by examiner

```
                       SEQUENCE LISTING

<160> NUMBER OF SEQ ID NOS: 45

<210> SEQ ID NO 1
<211> LENGTH: 107
<212> TYPE: PRT
<213> ORGANISM: Mus musculus

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 2
<211> LENGTH: 120
<212> TYPE: PRT
<213> ORGANISM: Mus musculus

<400> SEQUENCE: 2
```

-continued

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Ile Ile Ser Gly Ser Gly Gly Phe Thr Tyr Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Val Ala Pro Gly Thr Phe Asp Tyr Trp Gly Gln
            100                 105                 110

Gly Ala Leu Val Thr Val Ser Ser
        115                 120

<210> SEQ ID NO 3
<211> LENGTH: 107
<212> TYPE: PRT
<213> ORGANISM: Mus musculus

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys
            100                 105

<210> SEQ ID NO 4
<211> LENGTH: 120
<212> TYPE: PRT
<213> ORGANISM: Mus musculus

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Trp Tyr Asp Gly His Asp Lys Tyr Tyr Ser Tyr Tyr Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

-continued

```
Ala Arg Asp Ser Ser Trp Tyr Arg Tyr Phe Asp Tyr Trp Gly Gln
            100                 105                 110

Gly Thr Leu Val Thr Val Ser Ser
            115                 120

<210> SEQ ID NO 5
<211> LENGTH: 107
<212> TYPE: PRT
<213> ORGANISM: Mus musculus

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys
            100                 105

<210> SEQ ID NO 6
<211> LENGTH: 120
<212> TYPE: PRT
<213> ORGANISM: Mus musculus

<400> SEQUENCE: 6

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Trp Tyr Asp Gly His Asp Lys Tyr Tyr Ala Tyr Tyr Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Ser Trp Tyr Arg Tyr Phe Asp Tyr Trp Gly Gln
            100                 105                 110

Gly Thr Leu Val Thr Val Ser Ser
            115                 120

<210> SEQ ID NO 7
<211> LENGTH: 58
<212> TYPE: PRT
<213> ORGANISM: Mus musculus

<400> SEQUENCE: 7

Met Leu His Pro Leu Cys Lys Val Gly Ser His Gln Gly Ser Val Ala
1               5                   10                  15
```

-continued

Val Asp Leu Gly Gln Ile Ser Leu Ser Pro Ser Ala Ala Cys Ser Leu
            20                  25                  30

Lys Ile Leu Gln Leu Ile Thr Val Asn Ser Ile Ile Val Ser Leu Thr
        35                  40                  45

Phe Gly Gly Gly Thr Lys Val Glu Ile Lys
    50                  55

<210> SEQ ID NO 8
<211> LENGTH: 120
<212> TYPE: PRT
<213> ORGANISM: Mus musculus

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Trp Tyr Asp Gly His Asp Lys Tyr Tyr Ser Tyr Tyr Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Ser Ser Trp Tyr Arg Tyr Phe Asp Tyr Trp Gly Gln
            100                 105                 110

Gly Thr Leu Val Thr Val Ser Ser
        115                 120

<210> SEQ ID NO 9
<211> LENGTH: 57
<212> TYPE: PRT
<213> ORGANISM: Mus musculus

<400> SEQUENCE: 9

Met Pro Pro Val Trp Lys Val Gly Ser His Gln Ser Ala Ala Val
1               5                   10                  15

Asp Leu Gly Gln Ile Ser Leu Ser Pro Ser Ala Ala Cys Ser Leu Lys
            20                  25                  30

Ile Leu Gln Leu Ile Thr Val Asn Ser Leu Ile Val Thr Leu Thr Phe
        35                  40                  45

Gly Gly Gly Thr Lys Val Glu Ile Lys
    50                  55

<210> SEQ ID NO 10
<211> LENGTH: 116
<212> TYPE: PRT
<213> ORGANISM: Mus musculus

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Lys Asn Trp Ser Phe Asp Phe Trp Gly Gln Gly Thr Leu Val
                100                 105                 110

Thr Val Ser Ser
            115

<210> SEQ ID NO 11
<211> LENGTH: 106
<212> TYPE: PRT
<213> ORGANISM: Mus musculus

<400> SEQUENCE: 11

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Gly Val Ser Arg Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Val Ser Gly
         50                  55                  60

Ser Gly Pro Gly Thr Asp Phe Thr Leu Thr Ile Ser Ser Leu Glu Pro
 65                  70                  75                  80

Glu Asp Phe Ala Val Asp Tyr Cys Gln Gln Arg Ser Asn Trp Gln Tyr
                 85                  90                  95

Thr Phe Gly Gln Gly Thr Lys Leu Glu Ile
                100                 105

<210> SEQ ID NO 12
<211> LENGTH: 121
<212> TYPE: PRT
<213> ORGANISM: Mus musculus

<400> SEQUENCE: 12

Gln Lys Gln Leu Val Glu Phe Gly Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Val Ile Trp Asn Asp Gly Ser Asn Lys Tyr Tyr Val Asp Ser Val
         50                  55                  60

Lys Gly Arg Phe Ile Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Met Gly Ile Tyr Tyr Tyr Gly Met Asp Val Trp Gly
                100                 105                 110

Gln Gly Thr Thr Val Thr Val Ser Ser
            115                 120

<210> SEQ ID NO 13
<211> LENGTH: 107
<212> TYPE: PRT
```

<213> ORGANISM: Mus musculus

<400> SEQUENCE: 13

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 14
<211> LENGTH: 330
<212> TYPE: PRT
<213> ORGANISM: Homo sapiens

<400> SEQUENCE: 14

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

-continued

```
                  245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

-continued

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 16
<211> LENGTH: 104
<212> TYPE: PRT
<213> ORGANISM: Mus musculus

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Thr Phe
                85                  90                  95

Gly Gln Gly Thr Lys Val Glu Ile
            100

<210> SEQ ID NO 17
<211> LENGTH: 5
<212> TYPE: PRT
<213> ORGANISM: Mus musculus

<400> SEQUENCE: 17

Ser Tyr Thr Met His
1               5

<210> SEQ ID NO 18
<211> LENGTH: 5
<212> TYPE: PRT
<213> ORGANISM: Mus musculus

<400> SEQUENCE: 18

Ser Tyr Ala Met Ser
1               5

<210> SEQ ID NO 19
<211> LENGTH: 5
<212> TYPE: PRT
<213> ORGANISM: Mus musculus

<400> SEQUENCE: 19

Asn Phe Gly Met His
1               5

<210> SEQ ID NO 20
<211> LENGTH: 5
<212> TYPE: PRT
<213> ORGANISM: Mus musculus

<400> SEQUENCE: 20

```
Asn Tyr Gly Met His
1               5

<210> SEQ ID NO 21
<211> LENGTH: 17
<212> TYPE: PRT
<213> ORGANISM: Mus musculus

<400> SEQUENCE: 21

Ile Ile Ser Gly Ser Gly Gly Phe Thr Tyr Tyr Ala Asp Ser Val Lys
1               5                   10                  15

Gly

<210> SEQ ID NO 22
<211> LENGTH: 17
<212> TYPE: PRT
<213> ORGANISM: Mus musculus

<400> SEQUENCE: 22

Ala Ile Trp Tyr Asp Gly His Asp Lys Tyr Tyr Ser Tyr Tyr Val Lys
1               5                   10                  15

Gly

<210> SEQ ID NO 23
<211> LENGTH: 17
<212> TYPE: PRT
<213> ORGANISM: Mus musculus

<400> SEQUENCE: 23

Ala Ile Trp Tyr Asp Gly His Asp Lys Tyr Tyr Ala Tyr Tyr Val Lys
1               5                   10                  15

Gly

<210> SEQ ID NO 24
<211> LENGTH: 17
<212> TYPE: PRT
<213> ORGANISM: Mus musculus

<400> SEQUENCE: 24

Val Ile Trp Tyr Asp Gly Ser Asn Lys Tyr Tyr Val Asp Ser Val Lys
1               5                   10                  15

Gly

<210> SEQ ID NO 25
<211> LENGTH: 17
<212> TYPE: PRT
<213> ORGANISM: Mus musculus

<400> SEQUENCE: 25

Val Ile Trp Asn Asp Gly Ser Asn Lys Tyr Tyr Val Asp Ser Val Lys
1               5                   10                  15

Gly

<210> SEQ ID NO 26
<211> LENGTH: 11
<212> TYPE: PRT
<213> ORGANISM: Mus musculus

<400> SEQUENCE: 26

Asp Ser Ser Ser Trp Tyr Arg Tyr Phe Asp Tyr
1               5                   10
```

```
<210> SEQ ID NO 27
<211> LENGTH: 11
<212> TYPE: PRT
<213> ORGANISM: Mus musculus

<400> SEQUENCE: 27

Asp Arg Leu Val Ala Pro Gly Thr Phe Asp Tyr
1               5                   10

<210> SEQ ID NO 28
<211> LENGTH: 7
<212> TYPE: PRT
<213> ORGANISM: Mus musculus

<400> SEQUENCE: 28

Lys Asn Trp Ser Phe Asp Phe
1               5

<210> SEQ ID NO 29
<211> LENGTH: 12
<212> TYPE: PRT
<213> ORGANISM: Mus musculus

<400> SEQUENCE: 29

Asp Arg Met Gly Ile Tyr Tyr Tyr Gly Met Asp Val
1               5                   10

<210> SEQ ID NO 30
<211> LENGTH: 11
<212> TYPE: PRT
<213> ORGANISM: Mus musculus

<400> SEQUENCE: 30

Arg Ala Ser Gln Gly Ile Ser Ser Trp Leu Ala
1               5                   10

<210> SEQ ID NO 31
<211> LENGTH: 12
<212> TYPE: PRT
<213> ORGANISM: Mus musculus

<400> SEQUENCE: 31

Arg Ala Ser Gln Ser Val Ser Ser Ser Tyr Leu Ala
1               5                   10

<210> SEQ ID NO 32
<211> LENGTH: 12
<212> TYPE: PRT
<213> ORGANISM: Mus musculus

<400> SEQUENCE: 32

Arg Ala Ser Gln Ser Val Ser Ser Asn Tyr Leu Ala
1               5                   10

<210> SEQ ID NO 33
<211> LENGTH: 11
<212> TYPE: PRT
<213> ORGANISM: Mus musculus

<400> SEQUENCE: 33

Arg Ala Ser Gln Gly Val Ser Arg Tyr Leu Ala
1               5                   10

<210> SEQ ID NO 34
```

```
<211> LENGTH: 11
<212> TYPE: PRT
<213> ORGANISM: Mus musculus

<400> SEQUENCE: 34

Arg Ala Ser Gln Ser Val Ser Ser Tyr Leu Ala
1               5                   10

<210> SEQ ID NO 35
<211> LENGTH: 7
<212> TYPE: PRT
<213> ORGANISM: Mus musculus

<400> SEQUENCE: 35

Gly Ala Ser Ser Arg Ala Thr
1               5

<210> SEQ ID NO 36
<211> LENGTH: 7
<212> TYPE: PRT
<213> ORGANISM: Mus musculus

<400> SEQUENCE: 36

Ala Ala Ser Ser Leu Gln Ser
1               5

<210> SEQ ID NO 37
<211> LENGTH: 7
<212> TYPE: PRT
<213> ORGANISM: Mus musculus

<400> SEQUENCE: 37

Met Pro Pro Val Trp Lys Val
1               5

<210> SEQ ID NO 38
<211> LENGTH: 7
<212> TYPE: PRT
<213> ORGANISM: Mus musculus

<400> SEQUENCE: 38

Asp Ala Ser Asn Arg Ala Thr
1               5

<210> SEQ ID NO 39
<211> LENGTH: 7
<212> TYPE: PRT
<213> ORGANISM: Mus musculus

<400> SEQUENCE: 39

Leu His Pro Leu Cys Lys Val
1               5

<210> SEQ ID NO 40
<211> LENGTH: 8
<212> TYPE: PRT
<213> ORGANISM: Mus musculus

<400> SEQUENCE: 40

Asn Ser Leu Ile Val Thr Leu Thr
1               5

<210> SEQ ID NO 41
<211> LENGTH: 9
<212> TYPE: PRT
```

```
<213> ORGANISM: Mus musculus

<400> SEQUENCE: 41

Gln Gln Tyr Asn Ser Tyr Pro Tyr Thr
1               5

<210> SEQ ID NO 42
<211> LENGTH: 8
<212> TYPE: PRT
<213> ORGANISM: Mus musculus

<400> SEQUENCE: 42

Gln Gln Tyr Gly Ser Ser Phe Thr
1               5

<210> SEQ ID NO 43
<211> LENGTH: 9
<212> TYPE: PRT
<213> ORGANISM: Mus musculus

<400> SEQUENCE: 43

Gln Gln Arg Ser Asn Trp Gln Tyr Thr
1               5

<210> SEQ ID NO 44
<211> LENGTH: 7
<212> TYPE: PRT
<213> ORGANISM: Mus musculus

<400> SEQUENCE: 44

Gln Gln Arg Ser Asn Trp Thr
1               5

<210> SEQ ID NO 45
<211> LENGTH: 8
<212> TYPE: PRT
<213> ORGANISM: Mus musculus

<400> SEQUENCE: 45

Asn Ser Ile Ile Val Ser Leu Thr
1               5
```

ANTI-OX40L ANTIBODIES

This application claims benefit under 35 U.S.C. 119(e) of European Patent Applications No. EP 04022158.2 filed Sep. 17, 2004, and EP 04030546.8 filed Dec. 23, 2004, which are hereby incorporated by reference in their entirety.

FIELD OF THE INVENTION

This invention relates generally to anti-OX40L antibodies and, in particular, to anti-OX40L antibodies that do not bind complement factor C1q, pharmaceutical compositions and uses thereof. Preferably, these antibodies are human or humanized antibodies.

BACKGROUND OF THE INVENTION

Human OX40L (gp34, SwissProt P23510) is expressed on activated B cells and dendritic cells upon CD40/CD40L ligation, and on endothelial cells in inflammatory tissues (Review: Weinberg, A. D., *Trends Immunol.* 23 (2002) 102-109). It has first been isolated from HTLV-1 infected human leukemic cells (immortalization of these T-cells by generation of an autokrine loop with OX40). OX40L and antibodies against are mentioned e.g. in WO 95/12673; WO 95/21915; WO 99/15200; Baum, P. R., et al., *EMBO J.* 13 (1994) 3992-4001; Imura, A., et al., *Blood* 89 (1997) 2951-2958; Imura, A., et al., *J. Exp. Med.* 183 (1996) 2185-2195; Kjaergaard, J., et al., *J. Immunol.* 167 (2001) 6669-6677; Lane, P., *J. Exp. Med.* 191 (2000) 201-206; Mallett, S., and Barclay, A. N., *Immunol. Today* 12 (1991) 220-223; Mallett, S., et al., *EMBO J.* 9 (1990) 1063-1068; Ndhlovu, L. C., et al., *J. Immunol.* 167 (2001) 2991-2999; Ohshima, Y., et al., *J. Immunol.* 159 (1997) 3838-3848; Rogers, P. R., et al., *Immunity* 15 (2001) 445-455; Stüber, E., and Strober, W., *J. Exp. Med.* 183 (1996) 979-989; Stüber, E., et al., *Gastroenterology* 115 (1998) 1205-1215; Takahashi, Y., et al., *J. Virol.* 75 (2001) 6748-6757; Takasawa, N., et al., *Jpn. J. Cancer Res.* 92 (2001) 377-382; Taylor, L., and Schwarz, H., *J. Immunol. Meth.* 255 (2001) 67-72; Weinberg, A. D., et al., *Nature Medicine* 2 (1996) 183-189; Weinberg, A. D., et al., *Semin. Immunol.* 10 (1998) 471-480; Weinberg, A. D., *Trends Immunol.* 23 (2002) 102-109; Wu, T., et al., *Transplant. Proc.* 33 (2001) 217-218; Higgins, L. M., et al., *J. Immunol.* 162 (1999) 486-493; and Yoshioka, T., et al., *Eur. J. Immunol.* 30 (2000) 2815-2823. Human OX40L is the ligand for human OX40 (CD134) which is transiently expressed on activated CD4+ T cells. Engagement of OX40 by its ligand leads to a costimulatory signal for T cell activation. OX40/OX40L interaction is described to create a bidirectional signal (Matsumura, Y., et al., *J. Immunol.* 163 (1999) 3007-3011; Kotani, A., et al., *Immunol. Lett.* 84 (2002)1-7). Further OX40/OX40L interaction mediate adhesion of activated T-cell to endothelial cells in inflammatory tissues. As OX40L is only transiently expressed on activated B cells, DC and endothelial cells, antibodies to OX40L should selectively block T cell activation and endothelial cell adhesion during an inflammatory response but leave unactivated, peripheral T cells unaffected. Yoshioka, A., et al. (*Eur. J. Immunol.* 30 (2000) 2815-2823) demonstrated the therapeutic potential of a neutralizing anti-mOX40L mAb in a mouse model for rheumatoid arthritis. Administration of it dramatically ameliorated the disease severity. This antibody showed similar activities in other related disease models, e.g. inflammatory skin disease, experimental autoimmune disease (EAE), GVHD, urine inflammatory bowel disease (Yoshioka, A., et al., *Eur. J. Immunol* 30 (1999) 2815-2823; Salek-Ardakani, S., et al., *J. Exp. Med.* 198 (2003) 315-324; Burgess, J. K., et al., *J. Allergy Clin. Immunol.* 113 (2004) 683-689; Hoshino, A., et al., *Eur. J. Immunol.* 33 (2003) 861-869; Arestides, R. S., et al., *Eur. J. Immunol.* 32 (2002) 2874-2880; Nohara, C., et al., *J. Immunol.* 166 (2001) 2108-2115; Weinberg, A. D., et al., *J. Immunol.* 162 (1999) 1818-1826; Higgins, L. M., et al., *J. Immunol.* 162 (1999) 486-493; Humphreys, I. R., et al., *J. Exp. Med.* 198 (2003) 1237-1242; Akiba, H., et al., *J. Exp. Med.* 191 (2000) 375-380; Ishii, N., et al., *Eur. J. Immunol.* 33 (2003) 2372-2381; Blazar, B. R., et al., *Blood* 101 (2003) 3741-3748; Tsukada, N., et al., *Blood* 95 (2000) 2434-2439; Akiba, H., et al., *Biochem. Biophys. Res. Commun.* 251 (1998) 131-136.

Antibodies against OX40L have been investigated for their anti-inflammatory effects in various disease models (Sugamura, K., et al., *Nat. Rev. Immunol.* 4 (2004) 420-431). Tanaka, Y., et al, *Int. J. Cancer* 36, (1985) 549-555; Tozawa, H., et al., *Int. J. Cancer* 41 (1988) 231-238; and Miura, S., et al., *Mol. Cell. Biol.* 11 (1991) 1313-1325 describe mouse monoclonal antibodies named TARM-34 and TAG-34 that react with surface antigens of lines of human lymphocytes bearing a human T-cell leukemia virus type-I (HTLV-I). TAG-34 antibody is commercially available from MBL International Corporation. TAG-34 binds also to OX40L.

SUMMARY OF THE INVENTION

The invention relates to an antibody, preferably a monoclonal antibody, characterized in that said antibody binds OX40L, contains a Fc part from human origin and does not bind human complement factor C1q and/or human Fcγ receptor on NK cells.

The invention further relates to an antibody, preferably a monoclonal antibody characterized in that said antibody contains a Fc part from human origin, binds to OX40L and to denatured OX40L (in a Western Blot) in an antibody concentration of 100 ng. This antibody binds to the same OX40L polypeptide epitope as the epitope to which the monoclonal antibody LC.001 binds. Preferably this antibody does not bind human complement factor C1q and/or human Fcγ receptor on NK cells.

The antibody according to the invention is preferably characterized in that non-binding of the antibody to complement factor C1q refers to an ELISA assay measurement wherein the maximal binding (Bmax) of the antibody at a concentration of 10 µg/ml to C1q is 30% or lower, preferably 20% or lower compared to Bmax of antibody LC.001.

Preferably the antibody does not bind to human FcγRI, FcγRIIA and/or FcγRIIIA. Especially preferred, the antibody does not bind to human Fcγ receptor on NK effector cells.

The antibody according to the invention is preferably characterized in that non-binding of the antibody to Fcγ receptor on NK cells refers to assay wherein the maximal binding (Bmax) of the antibody at a concentration of 20 µg/ml to NK cells is 20% or lower, preferably 10% or lower compared to Bmax of antibody LC.001.

The antibody according to the invention is preferably characterized in that it does not bind to FcγRI. This means that the antibody is characterized by an $EC_{50}$ value which is five fold or more, preferably seven fold or more, such as eight fold or more compared to the $EC_{50}$ value of LC.001, when measured in an assay testing binding of the antibody in a concentration ranging from 0.078-10 µg/ml to a B-cell lymphoma cell lacking FcγRIIA and FcγIIB, but expressing recombinant FcγRI.

The antibody has new and inventive properties causing a benefit for a patient in the need of a therapy with antibodies against OX40L, especially for a patient suffering from inflammatory disorders, especially from rheumatoid arthritis, allergic asthma, and GvHD in transplantation (see also Sugamura, K., et al., *Nat. Rev. Immunol.* 4 (2004) 420-431).

The antibody according to the invention is preferably characterized as being an IgG4 antibody or an IgG1 antibody comprising at least one amino acid mutation, preferably in the human Fc part, causing non-binding to complement factor C1q and/or non-binding to human Fcγ receptor on NK cells.

The antibody according to the invention is preferably a chimeric, human or humanized antibody.

The antibody according to the invention is preferably characterized in that it does not activate complement factor C3.

The antibody according to the invention is preferably characterized by binding to OX40L with a $K_D$ value of less than $10^{-8}$ M ($10^{-12}$ to $10^{-8}$ M), more preferably by a $K_D$ range of $10^{-12}$ to $10^{-9}$ M in a BIAcore assay.

The antibody according to the invention is preferably characterized by being of human subclass IgG4. In a further preferred embodiment of the invention, the antibody is characterized by being of any IgG class, preferably being IgG1 or IgG4, containing at least one mutation in E233, L234, L235, G236, D270, N297, E318, K320, K322, A327, A330, P331 and/or P329 (numbering according to EU index). Especially preferred are the IgG1 mutations PVA236, L234A/L235A and/or GLPSS331 as well as the IgG4 mutation L235E. It is further preferred that the antibody of IgG4 subclass contains the mutation S228P or the mutation S228P and L235E (Angal, S., et al., *Mol. Immunol.* 30 (1993) 105-108).

The antibody according to the invention therefore is preferably an antibody of human subclass IgG1, containing one or more mutation(s) from PVA236, GLPSS331 and/or L234A/L235A (numbering according to EU index).

The antibody according to the invention preferably inhibits the interaction of OX40L with OX40 in an ELISA using immobilized OX40L (preferably biotinylated OX40L immobilized on a streptavidine surface) at a coating concentration of 0.5 μg/ml with an $IC_{50}$ value of no more than 4 nM. More preferred the $IC_{50}$ value is in the range of 1 to 4 nM.

The antibody according to the invention is preferably characterized in that it does not elicit complement-dependent cytotoxicity (CDC).

The antibody according to the invention is preferably characterized in that it does not elicit antibody-dependent cellular cytotoxicity (ADCC).

The antibody according to the invention is preferably characterized in that said antibody binds OX40L and that the antibody comprises a variable region independently selected from the group consisting of a) the light chain ($V_L$) variable domain defined by amino acid sequence SEQ ID NO: 1 and the heavy chain ($V_H$) variable domain defined by SEQ ID NO:2;

b) the light chain variable domain defined by amino acid sequence SEQ ID NO:3 and the heavy chain variable domain defined by SEQ ID NO:4;

c) the light chain variable domain defined by amino acid sequence SEQ ID NO:5 and the heavy chain variable domain defined by SEQ ID NO:6;

d) the light chain variable domain defined by amino acid sequence SEQ ID NO:7 and the heavy chain variable domain defined by SEQ ID NO:8;

e) the light chain variable domain defined by amino acid sequence SEQ ID NO:9 and the heavy chain variable domain defined by SEQ ID NO:10;

f) the light chain variable domain defined by amino acid sequence SEQ ID NO:11 or 16 and the heavy chain variable domain defined by SEQ ID NO:12 or an OX40L-binding fragment thereof.

The antibody according to the invention is preferably characterized in that the human light chain variable region comprises an amino acid sequence independently selected from the group consisting of SEQ ID NO:1, 3, 5, 7, 9, 11 and 16.

The antibody according to the invention is preferably characterized in that the human heavy chain variable region comprises an amino acid sequence independently selected from the group consisting of SEQ ID NO: 2, 4, 6, 8, 10 and 12.

The CDR regions of the heavy and light chains are shown in SEQ ID NO: 17-46.

The antibody according to the invention is preferably characterized in that the antibody comprises the light chain variable domain defined by amino acid sequence SEQ ID NO:1 and the heavy chain variable domain defined by SEQ ID NO:2.

The antibody according to the invention is preferably characterized in that the human heavy chain constant region comprises an amino acid sequence independently selected from the group consisting of SEQ ID NO: 14 and 15.

The antibody according to the invention is preferably characterized in that the antibody comprises a K-light chain constant region of SEQ ID NO: 13.

The antibody according to the invention is preferably characterized by comprising a variable light chain and a variable heavy chain, characterized in that the variable heavy chain comprises CDR1, CDR2 and CDR3 characterized in that CDR3 is selected from SEQ ID NOs: 26-29. It is especially preferred that CDR1 is selected from SEQ ID NOs: 17-20, CDR2 is selected from SEQ ID NOs: 21-25 and CDR3 is selected from SEQ ID NOs: 26-29.

The antibody according to the invention is preferably characterized by comprising a variable light chain and a variable heavy chain, characterized in that the variable light chain comprises CDR1, CDR2 and CDR3 characterized in that CDR3 is selected from SEQ ID NOs: 40-45. It is especially preferred that CDR1 is selected from SEQ ID NOs: 30-34, CDR2 is selected from SEQ ID NOs: 35-39 and CDR3 is selected from SEQ ID NOs: 40-45.

The antibody according to the invention is preferably characterized by comprising a variable heavy chain and a variable light chain, characterized in that the variable heavy chain comprises CDR1, CDR2 and CDR3 characterized in that CDR3 of the heavy chain is selected from SEQ ID NOs: 26-29 and CDR3 of the light chain is selected from SEQ ID NOs: 40-45. It is especially preferred that the variable heavy chain comprises CDR1 selected from SEQ ID NOs: 17-20, CDR2 selected from SEQ ID NOs: 21-25 and CDR3 selected from SEQ ID NOs: 26-29 and the variable light chain comprises CDR1 selected from SEQ ID NOs: 30-34, CDR2 selected from SEQ ID NOs: 35-39 and CDR3 selected from SEQ ID NOs: 40-45.

All CDRs are selected independently from each other. Preferred are the combinations of CDRs A further embodiment of the invention is an antibody binding to OX40L, characterized in that it is produced by cell line hu-Mab<hOX40L>LC.001, hu-Mab<hOX40L>LC.005, hu-Mab<hOX40L>LC.010, hu-Mab<hOX40L>LC.019, hu-Mab<hOX40L>LC.029 or hu-Mab<hOX40L>LC.033.

The antibody according to the invention is preferably characterized in that the antibody comprises CDRs independently selected from the group consisting of a) the light chain (V_L) variable CDRs of amino acid sequence SEQ ID NO:1 and the heavy chain (V_H) variable CDRs of SEQ ID NO:2;

b) the light chain variable CDRs of amino acid sequence SEQ ID NO:3 and the heavy chain variable CDRs of SEQ ID NO:4;

c) the light chain variable CDRs of amino acid sequence SEQ ID NO:5 and the heavy chain variable CDRs of SEQ ID NO:6;

d) the light chain variable CDRs of amino acid sequence SEQ ID NO:7 and the heavy chain variable CDRs of SEQ ID NO:8;

e) the light chain variable CDRs of amino acid sequence SEQ ID NO:9 and the heavy chain variable CDRs of SEQ ID NO:10;

f) the light chain variable CDRs of amino acid sequence SEQ ID NO:11 or 16 and the heavy chain variable CDRs of SEQ ID NO:12 or an OX40L-binding fragment thereof.

A further embodiment of the invention is a nucleic acid molecule encoding an antibody molecule, a variable chain or a CDR domain thereof according to the invention.

CDRs on each chain are separated by framework amino acids.

In a preferred embodiment of the invention the antibody is a Fab, F(ab')$_2$ or a single-chain fragment.

A further embodiment of the invention is a vector comprising the nucleic acid molecule according to the invention.

A further embodiment of the invention is a host cell comprising the vector according to the invention.

A further embodiment of the invention is a method for the preparation of an antibody according to the invention comprising culturing the host cell according to the invention under conditions that allow synthesis of said antibody molecule and recovering said antibody molecule from said culture.

A further embodiment of the invention is a composition, preferably a pharmaceutical or a diagnostic composition of the antibody according to the invention.

A further embodiment of the invention is a pharmaceutical composition comprising an antibody according to the invention and at least one pharmaceutically acceptable excipient.

A further embodiment of the invention is a method for the treatment of a patient in need of therapy, characterized by administering to the patient a therapeutically effective amount of an antibody according to the invention.

A further embodiment of the invention is the use of an antibody according to the invention for therapy, preferably for the treatment of inflammatory diseases, especially for the treatment and/or prevention of rheumatoid arthritis, asthma and GvHD (graft versus host disease).

A further embodiment of the invention is the use of an antibody according to the invention for the preparation of a medicament for the prophylaxis and/or treatment of inflammatory disorders, preferably for the treatment of rheumatoid arthritis, asthma and GvHD.

A further embodiment of the invention is a diagnostic kit comprising an antibody according to the invention, a nucleic acid molecule according to the invention, a vector according to the invention or a host cell according to the invention.

DESCRIPTION OF THE SEQUENCE LISTING

Figure 1A:
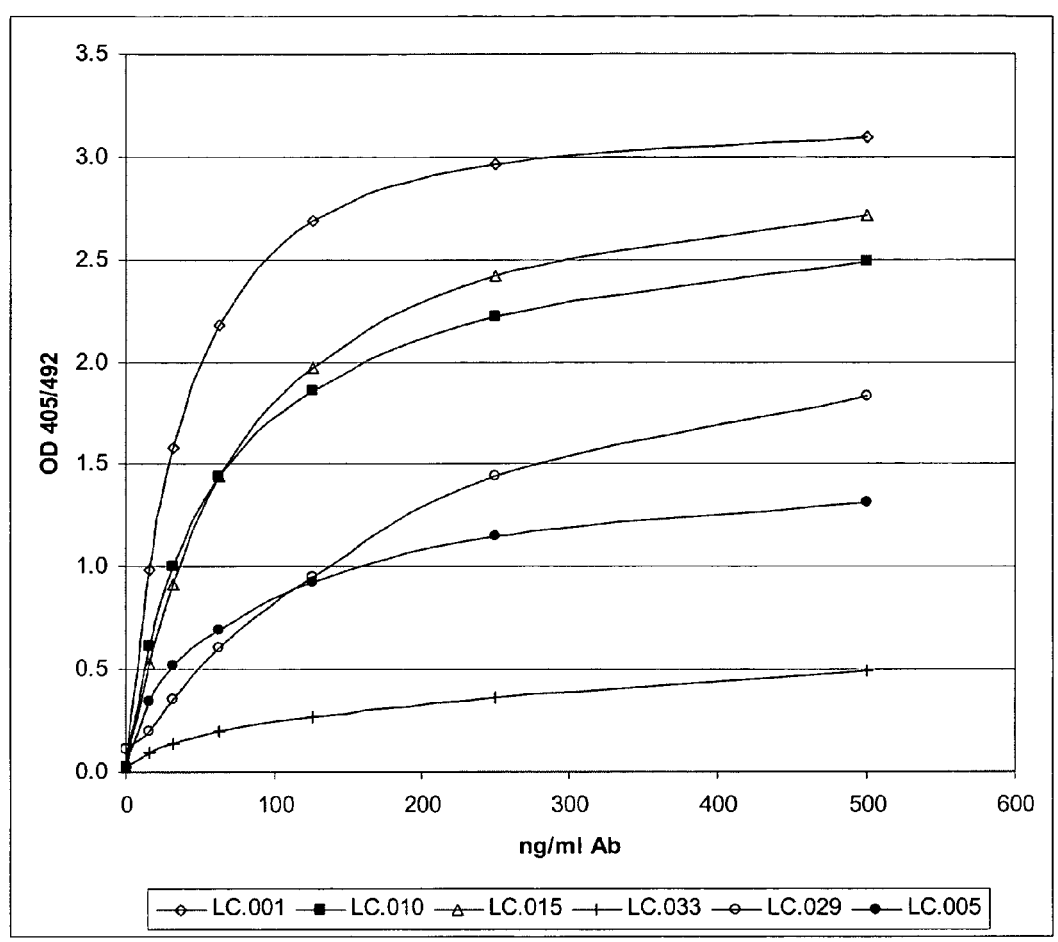
FIG. 1a shows "binding ELISA" for TAG-34, LC.001, LC.005, LC.010, LC.019, LC.029, LC.033.

SEQ ID NO:1 kappa light chain, variable region of LC.001
SEQ ID NO:2 γ heavy chain variable region of LC.001
SEQ ID NO:3 kappa light chain, variable region of LC.005
SEQ ID NO:4 γ heavy chain variable region of LC.005
SEQ ID NO:5 kappa light chain, variable region of LC.010
SEQ ID NO:6 γ heavy chain variable region of LC.010
SEQ ID NO:7 kappa light chain, variable region of LC.029
SEQ ID NO:8 γ heavy chain variable region of LC.029
SEQ ID NO:9 kappa light chain, variable region of LC.019
SEQ ID NO:10 γ heavy chain variable region of LC.019'
SEQ ID NO:11 kappa light chain, variable region of LC.033
SEQ ID NO:12 γ heavy chain variable region of LC.033
SEQ ID NO:13 kappa light chain constant region
SEQ ID NO:14 γ1 heavy chain constant region
SEQ ID NO:15 γ4 heavy chain constant region
SEQ ID NO:16 kappa light chain, mutant variable region of LC.033
SEQ ID NO:17-45 CDR sequences

DETAILED DESCRIPTION OF THE INVENTION

The term "OX40L" refers to a type II membrane protein belonging to the TNF-ligand family. Further names are ACT-4 receptor, CD134L, gp34 or TNF4_Human. It has a molecular weight of 34 KDa and is stored in SwissProt with the accession number P23510.

The term "OX40" confers to the receptor which binds to OX40L. It is a type I membrane protein belonging to the TNF receptor family. Further names are ACT-4, OX40L receptor, CD134 antigen, ACT35 antigen, TNR4_Human. It has a molecular weight of 50 kDa and is stored in SwissProt with the accession number P43489.

The term "antibody" encompasses the various forms of antibodies, preferably monoclonal antibodies including but not being limited to whole antibodies, antibody fragments, human antibodies, chimeric antibodies, humanized antibodies and genetically engineered antibodies (variant or mutant antibodies) as long as the characteristic properties according to the invention are retained. Especially preferred are human or humanized monoclonal antibodies, especially as recombinant human antibodies.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies." Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., *Proc. Natl. Acad. Sci. USA* 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., *Nature* 332 (1988) 323-327; and Neuberger, M. S., et al., *Nature* 314 (1985) 268-270. Particularly preferred CDRs correspond to those representing sequences recognizing the antigens noted above for chimeric and bifunctional antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Bruggemann, M., et al., *Year Immunol.* 7 (1993) 3340). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., *Monoclonal Antibodies and Cancer Therapy*, Alan R. Liss, p. 77 (1985); and Boerner, P., et al., *J. Immunol.* 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation). In addition the invention comprises monoclonal human antibodies against OX40L which bind to C1q and/or FcR. Such human antibodies are characterized by a high selectivity for human OX40L vs. mouse OX40L (>30 fold lower binding to mouse OX40L than to human OX40L) and do not show unspecific binding to TNFα or CD40L up to a concentration of 500 nM. Such antibodies are useful for generation of antibodies which do not bind C1q and/or FcR.

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

The "variable region" (variable region of a light chain ($V_L$), variable region of a heavy chain ($V_H$)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

The term "nucleic acid or nucleic acid molecule", as used herein, is intended to include DNA molecules and RNA molecules. A nucleic acid molecule may be single-stranded or double-stranded, but preferably is double-stranded DNA.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The "constant domains" are not involved directly in binding an antibody to an antigen, but exhibit various effector functions. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1 and IgA2. The heavy chain constant regions that correspond to the different classes of immunoglobulins are called $\alpha$, $\epsilon$, $\gamma$, and $\mu$, respectively. The antibodies according to the invention are preferably of IgG type.

The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T. J., et al., *J. Immunol.* 127 (1981) 2555-2560; Brunhouse, R., and Cebra, T. J., *Mol. Immunol.* 16 (1979) 907-917; Burton, D. R., et al., *Nature* 288 (1980) 338-344; Thommesen, J. E., et al., *Mol. Immunol.* 37 (2000) 995-1004; Idusogie, E. E., et al., *J. Immunol.* 164 (2000) 4178-4184; Hezareh, M., et al., *J. Virol.* 75 (2001) 12161-12168; Morgan, A., et al., *Immunology* 86 (1995) 319-324; and EP 0 307 434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation, C1q binding and C3 activation, whereas IgG4 do not activate the complement system, do not bind C1q and do not activate C3. As used herein the term "Fc part derived from human origin" denotes a Fc part which is either a Fc part of a human antibody of the subclass IgG4 or a Fc part of a human antibody of the subclass IgG1, IgG2 or IgG3 which is modified in such a way that no C1q binding, C3 activation and/or FcR binding as defined below can be detected. A "Fc part of an antibody" is a term well known to the skilled artisan and defined on the basis of papain cleavage of antibodies. The antibodies according to the invention contain as Fc part, preferably a Fc part derived from human origin and preferably all other parts of the human constant regions. Preferably the Fc part is a human Fc part and especially preferred either from human IgG4 subclass, preferably mutated in the hinge region (e.g. S228P and/or L235E) or a mutated Fc part from human IgG1 subclass. Mostly preferred are Fc parts comprising a heavy chain constant regions selected from the regions shown in SEQ ID NO: 14 and 15, SEQ ID NO: 14 with mutations L234A and L235A or SEQ ID NO: 15 with mutation S228P or mutations S228P and L235E.

The present invention refers to an antibody that binds OX40L and does not bind complement factor C1q, and/or Fc receptor. In a preferred embodiment of the invention, these antibodies do not elicit the complement dependent cytotoxicity (CDC) and/or antibody-dependent cellular cytotoxicity (ADCC). Preferably, this antibody is characterized in that it binds OX40L, contains a Fc part derived from human origin and does not bind complement factor C1q. More preferably, this antibody is a human or humanized monoclonal antibody.

The effector functions mediated by the Fc part of the antibody Fc region refer to effector functions that operate after the binding of an antibody to an antigen (these functions involve the activation of the complement cascade and/or cell activation by a Fc receptor).

The function of the complement cascade can be assessed by the CH50 assay. Sheep red cells sensitized with anti-red cell antibodies (EA) are added to test serum to activate the classical pathway resulting in haemolysis. The volume of serum needed to lyse 50% of the red cells determines the CH50 unit. The $\Delta$P-CH50 measures the alternative and the terminal pathways. The procedure is similar except that rabbit red cells are used. The alternative pathway is activated upon addition of test serum.

C1q and two serine proteases, C1r and C1s, form the complex C1, the first component of the complement dependent cytotoxicity (CDC) pathway. To activate the complement cascade C1q binds to at least two molecules of IgG1 or one molecule of IgM, attached to the antigenic target (Ward, E. S., and Ghetie, V., *Ther. Immunol.* 2 (1995) 77-94). Burton, D. R., described (*Mol. Immunol.* 22 (1985) 161-206) that the heavy chain region comprising amino acid residues 318 to 337 is being involved in complement fixation. Duncan, A. R., and Winter, G. (*Nature* 332 (1988) 738-740), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

The term "complement-dependent cytotoxicity (CDC)" refers to lysis of OX40L expressing human endothelial cells by the antibody according to the invention in the presence of complement. CDC is measured preferably by the treatment of OX40L expressing human endothelial cells with an antibody according to the invention in the presence of complement. The cells are preferably labeled with calcein. CDC is found if the antibody induces lysis of 20% or more of the target cells at a concentration of 30 µg/ml. The inventors have found that for the properties of the antibodies according to the invention reduced binding to the complement factor C1q in an ELISA assay is essential. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm ($OD_{405}$) for peroxidase substrate ABTS® (2,2'-azino-di-[3-ethylbenz-thiazoline-6-sulfonate (6)]. Accordingly the present invention refers to an antibody, characterized in that non-binding of the antibody to complement factor C1q refers to such an ELISA assay measurement wherein the maximal binding (Bmax) of C1q to an antibody according to the invention at a concentration of 10 µg/ml of the antibody is 20% or lower of Bmax observed with antibody LC.001, preferably 10% or lower.

It is further preferred, that an antibody according to the invention shows a reduced activation of complement factor C3 in an ELISA assay. The assay is performed in the same manner as the C1q assay. In such an assay in principle an ELISA plate is coated with concentration ranges of the antibody, to which human serum is added. C3 binding is detected by an antibody directed against C3 followed by a peroxidase-labeled conjugate. Detection of binding (maximal binding Bmax) is measured as optical density at 405 nm ($OD_{405}$) for peroxidase substrate ABTS®. Accordingly the present invention refers to an antibody, characterized in that non-binding of the antibody to complement factor C3 refers to such an ELISA assay measurement wherein the maximal binding (Bmax) of C3 to the antibody at a concentration of 10 µg/ml of the antibody is 10% of Bmax of antibody LC.001 preferably 5% or lower.

The term "antibody-dependent cellular cytotoxicity (ADCC)" is a function mediated by Fc receptor binding and refers to lysis of OX40L expressing target cells by an antibody according to the invention in the presence of effector cells. ADCC is measured preferably by the treatment of a preparation of OX40L expressing erythroid cells (e.g. K562 cells expressing recombinant human OX40L) with an antibody according to the invention in the presence of effector cells such as freshly isolated PBMC (peripheral blood mononuclear cells) or purified effector cells from buffy coats, like monocytes or NK (natural killer) cells. Target cells are labeled with $^{51}Cr$ and subsequently incubated with the antibodies. The labeled cells are incubated with effector cells and the supernatant is analyzed for released $^{51}Cr$. Controls include the incubation of the target endothelial cells with effector cells but without the antibody. The capacity of the antibodies to induce the initial steps mediating ADCC was investigated by measuring their binding to Fcγ receptors expressing cells, such as cells, recombinantly expressing FcγRI and/or FcγIIA or NK cells (expressing essentially FcγRIIIA). Preferably binding to FcγR on NK cells is measured.

Fc receptor binding effector functions can be mediated by the interaction of the Fc region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC). Van de Winkel, J. G., and Anderson, C. L., *J. Leukoc. Biol.* 49 (1991) 511-524). FcRs are defined by their specificity for immunoglobulin isotypes; Fc receptors for IgG antibodies are referred to as FcγR, for IgE as FcεR, for IgA as FcαR and so on. Fc receptor binding is described e.g. in Ravetch, J. V., and Kinet, J. P., *Annu. Rev. Immunol.* 9 (1991) 457-492; Capel, P. J., et al., *Immunomethods* 4 (1994) 25-34; de Haas, M., et al., *J Lab. Clin. Med.* 126 (1995) 330-341; and Gessner, J. E., et al., *Ann. Hematol.* 76 (1998) 231-248.

Cross-linking of receptors for the Fc domain of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in IgG of at least one of E233-G236, P238, D265, N297, A327 and P329 reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al. *Eur. J. Immunol.* 29 (1999) 2613-2624).

FcγRII (CD32) binds complexed IgG with medium to low affinity and is widely expressed. These receptors can be divided into two important types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to say for example the IgE class. On macrophages, FcγRIIB acts to inhibit phagocytosis as mediated through FcγRIIA. On eosinophils and mast cells the b form may help to suppress activation of these cells through IgE binding to its separate receptor. Reduced binding for FcγRIIA is found e.g. for IgG mutation of at least one of E233-G236, P238, D265, N297, A327, P329, D270, Q295, A327, R292 and K414.

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for mutation of at least one of E233-G236, P238, D265, N297, A327, P329, D270, Q295, A327, S239, E269, E293, Y296, V303, A327, K338 and D376.

Mapping of the binding sites on human IgG1 for Fc receptors, the above mentioned mutation sites and methods for measuring binding to FcγRI and FcγRIIA are described in Shields, R. L., et al., *J. Biol. Chem.* 276 (2001) 6591-6604.

The term "Fc receptor" when used herein, refer to activation receptors characterized by the presence of a cytoplasmatic ITAM sequence associated with the receptor (see e.g. Ravetch, J. V., and Bolland, S., *Annu. Rev. Immunol.* 19 (2001) 275-290). Such receptors are FcγRI, FcγRIIA and FcγRIIIA. The antibodies according to the invention preferably show a reduced binding to Fcγ receptors, preferably to FcγIIA. Preferably the term "no binding of FcγR" means that in an antibody concentration of 10 µg/ml the binding of an antibody according to the invention to NK cells is 10% or less of the binding found for antibody LC.001.

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al. *J. Biol.*

Chem. 276 (2001) 6591-6604; Lund, J., et al. *FASEB J.* 9 (1995) 115-119; Morgan, A., et al., *Immunology* 86 (1995) 319-324; and EP 0 307 434). Preferably an antibody according to the invention of IgG1 or IgG2 subclass comprises mutation PVA236, GLPSS331 and/or L234A/L235A. An antibody according to the invention of IgG4 subclass comprises preferably mutation L235E. Further preferred IgG4 mutations are S228P or L235E and S228P (cf. table 1).

The term "binding to OX40L" as used herein means the binding of the antibody to human OX40L in a BIAcore assay (Pharmacia Biosensor AB, Uppsala, Sweden). For further confirmation, binding to OX40L can also be determined in an ELISA in which purified OX40L is coated to microtiter plates, or in a FACS— assay in which direct or indirect labeled antibody is bound to K562 cells expressing OX40L.

In the BIAcore assay the antibody is bound to a surface and binding of OX40L is measured by Surface Plasmon Resonance (SPR). The affinity of the binding is defined by the terms ka (rate constant for the association of the antibody to the antigen), kd (rate constant for the dissociation), and $K_D$ (kd/ka). The antibodies according to the invention show a $K_D$ of $10^{-8}$ or less, preferably of about $10^{-12}$ to $10^{-9}$ M (see examples). Accordingly, the present invention refers to an antibody as described above, wherein the antibody bind to OX40L with a $K_D$ value of less than 1-8 M in a BIAcore assay, preferably wherein the $K_D$ range is $10^{-12}$ to $10^{-9}$ M.

In the OX40L-specific binding ELISA, OX40L is coated onto microtiter plates and the binding of the antibody to OX40L is detected with a HRP-conjugated anti-human IgG and the usual steps of an ELISA. The $EC_{50}$ values in this assay are preferably in the range between 3 nM and 8 nM.

The term "inhibiting the binding of OX40 to OX40L" as used herein refers to the binding of the antibody described in the present invention to human OX40L, thereby inhibiting the OX40/OX40L interaction, and thereby inhibiting the OX40L induced signal transduction.

The antibodies of the present invention inhibit hOX40L/OX40 interaction preferably i) at the in vitro level shown by an ELISA assay by blocking the interaction of biotinylated, immobilized OX40L with soluble OX40 by the antibody at a (solid phase) coating concentration of 0.5 μg/ml biotinylated OX40L with an $IC_{50}$ value in the range of 1 nM-4 nM, ii) at the in vitro level shown by a Biacore assay by blocking the interaction of immobilized OX40 with soluble OX40L (10 nM, preferably as hOX40L-His) by the antibody at an antibody concentration of 0.78-100 nM with an $IC_{50}$ value in the range of 1 nM-10 nM, iii) on the cellular level shown by a FACS-assay in which the antibody blocks the interaction of K562 cells expressing OX40L (K562_OX40L) in a concentration of $2 \times 10^5$ cells/sample with OX40 with an $IC_{50}$ value in the range of 4-20 nM, iv) by an OX40-signal transduction assay in which the antibody blocks the OX40 signal transduction induced by K562_OX40L, into $3 \times 10^4$ HeLa-cells expressing OX40 per sample, which results in a blocking of NFκB activation with an $IC_{50}$ value in the range of 1-5 mM, v) by a T-cell activation assay, in which the antibody blocks OX40L induced T-cell activation by K562_OX40L at a concentration of $1.5 \times 10^5$ cells/sample and a PHA concentration of 0.75 μg/ml with an IC50 value in the range of 1 nM to 10 nM, and/or vi) by a T-cell activation assay, in which the antibody blocks OX40L induced T cell activation by activated B cells or dendritic cells (Tetanus assay) at an antibody concentration of 10 μg/ml, inhibition of 40%-60% was obtained.

Antibodies showing in an ELISA assay inhibition by blocking the interaction of immobilized OX40L with soluble OX40 at a coating concentration of 0.5 μg/ml OX40L with an IC50 value in the range of 1 nM-4 nM are preferred.

Accordingly, a further preferred embodiment of the present invention refer to an antibody, characterized in that said antibody, thereby inhibiting the OX40/OX40L interaction, and thereby inhibiting the OX40L induced signal transduction.

It is further preferred, that an antibody according to the invention does not show unspecific binding to TNFalpha and CD40L up to a concentration of 500 nM of TNFalpha or CD40L.

It is further preferred, that an antibody according to the invention show at least 30 fold lower binding to mouse OX40L compared to human OX40L.

It is further preferred, that an antibody according to the invention in a concentration of 10 μg/ml do not induce down-regulation of OX40L expression on HUVEC cells.

In a further preferred embodiment, the antibodies of the present invention are characterized in that they comprise a variable domain combination independently selected from the group consisting of combinations a) the light chain variable domain of antibody LC.001 defined by amino acid sequence SEQ ID NO:1 and the heavy chain variable domain of antibody LC.001 defined by SEQ ID NO:2;

b) the light chain variable domain of antibody LC.005 defined by amino acid sequence SEQ ID NO:3 and the heavy chain variable domain of the antibody LC.005 defined by SEQ ID NO:4;

c) the light chain variable domain of antibody LC.010 defined by amino acid sequence SEQ ID NO: 5 and the heavy chain variable domain of the antibody LC.010 defined by SEQ ID NO:6;

d) the light chain variable domain of antibody LC.029 defined by amino acid sequence SEQ ID NO:7 and the heavy chain variable domain of antibody LC.029 defined by SEQ ID NO:8;

e) the light chain variable domain of antibody LC.019 defined by amino acid sequence SEQ ID NO:9 and the heavy chain variable domain of the antibody LC.019 defined by SEQ ID NO:10;

f) the light chain variable domain of antibody LC.033 defined by amino acid sequence SEQ ID NO:11 OR 16 and the heavy chain variable domain of the antibody LC.033 defined by SEQ ID NO:12.

In an further preferred embodiment, the antibodies of the present invention are characterized in that they comprise a constant region independently selected from the group consisting of g) the light/kappa chain defined by sequence SEQ ID NO:13;

h) the heavy/gamma chain of the IgG1 isotype SEQ ID NO:14 with one or more mutations selected from L234A and L235A, PVA236 or GLPSS331;

i) the heavy/gamma chain of the IgG4 isotype SEQ ID NO:15;

j) the heavy/gamma chain of the IgG4 isotype SEQ ID NO:15 with the mutation S228P or mutations S228P and L235E. Further preferred are all combinations of each variable antibody domain combination a)-f) together with a gamma chain h), i) or j) and preferably with a kappa chain g).

Especially preferred are antibodies comprising the variable chains of antibodies LC.001, LC.005, LC.010, LC.019, LC.029 or LC.033 each with kappa chain defined by sequence SEQ ID NO:13 and the heavy/gamma chain of the IgG1 isotype SEQ ID NO:14 with the mutations L234A and L235A, antibodies comprising the variable chains of antibodies LC.001, LC.005, LC.010, LC.019, LC.029 or LC.033 each with kappa chain defined by sequence SEQ ID NO:13 and the heavy/gamma chain of the IgG4 isotype SEQ ID NO:15, antibodies comprising the variable chains of antibodies LC.001, LC.005, LC.010, LC.019, LC.029 or LC.033 each with kappa chain defined by sequence SEQ ID NO:13 and the heavy/gamma chain of the IgG4 isotype SEQ ID NO:15 with the mutation S228P.

Preferably, the antibodies comprise the light chain variable CDR of amino acid sequence SEQ ID NO:1 and the heavy chain variable CDR of SEQ ID NO:2.

The preferred antibodies are characterized in that the antibodies are of human IgG4 subclass or of another human subclass (preferably IgG1) comprising at least one amino acid mutation causing non-binding to complement factor C1q and/or loss of FCR binding. Such preferred variant antibodies comprise for example the amino acid sequence SEQ ID NO:14 with the mutations L234A and L235A or SEQ ID NO:15 with or without mutation S228P.

Preferred antibodies according to the invention are antibodies defined as IgG1 v1 (PVA-236; GLPSS331 as specified by E233P; L234V; L235A; delta G236; A327G; A330S; P331S), IgG1v2 (L234A; L235A) and IgG4v1 (S228P; L235E) and IgG4x (S228P).

Hybridoma cell line hu-Mab<hOX40L>LC.001 according to the invention was deposited, under the Budapest Treaty on the international recognition of the deposit of microorganisms for the purposes of patent procedure, with Deutsche Sammlung von Mikroorganismen und Zellkulturen GmbH (DSMZ), Inhoffenstraße 7 B, 38124 Braunschweig, Germany on 27, Jul. 2004 under Deposition No. DSM ACC 2672.

Hybridoma cell lines hu-Mab<hOX40L>LC.005 (DSM ACC 2685), hu-Mab<hOX40L>LC.010 (DSM ACC 2686), hu-Mab<hOX40L>LC.019, hu-Mab<hOX40L>LC.029 (DSM ACC 2688) and hu-Mab<hOX40L>LC.033 (DSM ACC 2689) according to the invention were deposited, under the Budapest Treaty on the international recognition of the deposit of microorganisms for the purposes of patent procedure, with Deutsche Sammlung von Mikroorganismen und Zellkulturen GmbH (DSMZ), Inhoffenstraße 7 B, 38124 Braunschweig, Germany on 2, Sep. 2004.

The antibodies obtainable from said cell lines are preferred embodiments of the invention and especially useful as intermediate substances for the generation of antibodies according to the invention not binding complement factor C1q and/or not binding to human Fcγ receptor.

Further preferred embodiments of the invention are isolated anti-OX40L antibodies which bind to OX40L and bind to the same OX40L-epitope to which also monoclonal antibodies LC.005, LC.010 or LC.029 produced by the hybridoma cell lines deposited bind.

A further embodiment of the invention is a method for the production of an antibody against OX40L which do not bind human complement factor C1q and/or human Fcγ receptor characterized in that the sequence of a nucleic acid encoding the heavy chain of an antibody binding to OX40L with a $K_D$ value of less than $10^{-8}$ M is modified in such a manner that said modified antibody does not bind complement factor C1q and/or human Fcγ receptor on NK cells, said modified nucleic acid and the nucleic acid encoding the light chain of said antibody are inserted into an expression vector, said vector is inserted in a prokaryotic or eukaryotic host cell, the encoded protein is expressed and recovered from the host cell or the supernant.

A further embodiment of the invention is a method for the production of an antibody according to the invention not binding complement factor C1q and/or not binding to human Fcγ receptor characterized in that an antibody obtainable from one of said cell lines is modified by "class switching", i.e. change or mutation of the Fc part (e.g. from IgG1 to IgG4 and/or IgG1/IgG4 mutation) preferably defined as IgG1 v1 (PVA-236; GLPSS331 as specified by E233P; L234V; L235A; delta G236; A327G; A330S; P331S), IgG1v2 (L234A; L235A) and IgG4v1 (S228P; L235E) and IgG4x (S228P).

In a further preferred embodiment, these antibodies also comprise antibody fragments selected from the group consisting of Fab, F(ab')$_2$ and single-chain fragments.

A "variant" anti-OX40L antibody, refers therefore herein to a molecule which differs in amino acid sequence from a "parent" anti-OX40L antibody amino acid sequence by virtue of addition, deletion and/or substitution of one or more amino acid residue(s) in the parent antibody sequence. In the preferred embodiment, the variant comprises one or more amino acid substitution(s) in one or more constant or variable region(s) of the parent antibody, preferably in the constant region. For example, the variant may comprise at least one, e.g. from about one to about ten, and preferably from about two to about five, substitutions in one or more variable regions of the parent antibody. Ordinarily, the variant will have an amino acid sequence having at least 90% amino acid sequence identity with the parent antibody constant and/or variable domain sequences, more preferably at least 95%, and most preferably at least 99%.

Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human OX40L and preferably has properties, which are superior to those of the parent antibody. For example, the variant may have reduced side effects during treatment of rheumatoid arthritis and asthma as the OX40L is not only transiently expressed on B-cells, Dendritic cells and macrophages, but also on endothelial cells (Kotani, A., et al., Immunol. Lett. 84 (2002)1-7), airway smooth muscle cells (=ASM) (Burgess, J. K., J. Allergy Clin. Immunol 113 (2004) 683-689) and microglial cells (Weinberg, A. D., et al., J. Immunol. 162 (1999) 1818-1826). Binding of the antibodies against OX40L to endothelial cells, ASM and Microglial cells can result in cell damage and of endothelial cells resulting in vascular leakage, of ASM cells resulting in lung destruction, of microglial cells resulting in damages of the microglia.

The "parent" antibody herein is one, which is encoded by an amino acid sequence used for the preparation of the variant. Preferably, the parent antibody has a human framework region and, if present, has human antibody constant region(s). For example, the parent antibody may be a humanized or human antibody, preferably of IgG1 type.

The antibodies according to the invention include, in addition, such antibodies having "conservative sequence modifications", nucleotide and amino acid sequence modifications, which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-OX40L antibody can be preferably replaced with another amino acid residue from the same side chain family.

Amino acid substitutions can be performed by mutagenesis based upon molecular modeling as described by Riechmann, L., et al., *Nature* 332 (1988) 323-327 and Queen, C., et al., *Proc. Natl. Acad. Sci. USA* 86 (1989) 10029-10033.

The invention further comprises a method for the production of an antibody, characterized in that the sequence of a first nucleic acid encoding the heavy chain of an antibody binding to OX40L with a $K_D$ value of less than $10^{-8}$ M is modified in such a manner that said modified antibody do not bind complement factor C1q and/or human Fcγ receptor on NK cells, said modified first nucleic acid and a second nucleic acid encoding the light chain of said antibody are inserted into an expression vector, said vector is inserted in a prokaryotic or eukariotic host cell, culturing said host cell under conditions that allow synthesis of said antibody and recovering said antibody from said culture.

The invention further comprises a method for the production of an antibody according to the invention and comprising a Fc part derived from human origin, said method comprising the steps of a) transforming a host cell with a first nucleic acid sequence encoding a light chain of a parent human antibody according to the invention and a second DNA sequence encoding a heavy chain of said parent human antibody wherein the Fc part is modified in that said Fc part does not bind complement factor C1q and/or Fc receptor; b) expressing said first and second DNA sequence so that said antibody heavy and light chains are produced and c) recovering said antibody from the host cell or host cell culture.

The present invention also comprises nucleic acid molecules encoding an antibody mentioned above, the corresponding vectors comprising these nucleic acids and the corresponding host cell for these vectors. The invention encompasses a method for the preparation of the antibodies comprising culturing the corresponding host cells under conditions that allow synthesis of said antibody molecules and recovering said antibodies from said culture, e.g. by expressing a nucleic acid encoding a heavy chain and a nucleic acid encoding a light chain in a prokaryotic or eukaryotic host cell and recovering said polypeptide from said cell.

Diagnostic and therapeutic uses for the antibody are contemplated. In one diagnostic application, the invention provides a method for determining the presence of the OX40L protein comprising exposing a sample suspected of containing OX40L to the anti-OX40L antibody and determining binding of the antibody to the sample. The OX40L protein may be inserted into the cell membran of OX40L-expressing cells by its transmembrane domain or may occur as soluble extracellular domain in body fluids released by mechanisms like shedding or proteolytic release. For this use, the invention provides a kit comprising the antibody and instructions for using the antibody to detect the OX40L protein.

The antibodies of the present invention are useful for prevention and/or treatment of inflammatory diseases in a mammal, preferably a patient suspected of having or suffering of such a disease. Such diseases include allergic reactions such as asthma. Other applications are the treatment of autoimmune diseases including rheumatoid arthritis.

The invention further provides a method for treating a mammal suffering from the above mentioned inflammatory disorders, especially from asthma and rheumatoid arthritis.

Preferably the antibodies of the present invention can be used for the treatment of severe persistent asthma in patients whose symptoms are not adequately controlled with inhaled corticosteroids. The patient population includes adults and adolescents (12 years of age and older) with inadequately controlled severe persistent asthma. The antibody will be delivered preferably subcutaneously once or twice a month. Main endpoint will be preferably decrease in acute exacerbations. Other endpoints include peak flow, daytime asthma symptoms, nocturnal awakenings, quality of life, emergency room visits, asthma free days, beta-2 agonist use, steroid reduction or tapering and effect on hyper-responsiveness.

It is further preferred to use the antibodies according to the invention for monotherapy or in combination with methotrexate or other DMARDs (Disease Modifying Anti-Rheumatic Drugs) for the treatment of adults with moderate to severe active rheumatoid arthritis. It will be administered as subcutaneous injection every 2 or 4 weeks. It will be chronic therapy in patients who have failed one or more DMARDs. Endpoints will include reduction in signs and symptoms and the inhibition of progression of structural damage in adult patients with active rheumatoid arthritis. Prevention of disability, improvement in signs and symptoms measured by ACR criteria (ACR20>60%, ACR50>35%, ACR70>15%; index from the American College of Rheumatology; www.rheumatology.com).

A further embodiment of the invention is the use of the antibodies according to the invention for the manufacture of medicaments for the treatment of these diseases.

The invention relates also to the use of the antibodies as defined above for the manufacture of a pharmaceutical composition and comprises a pharmaceutical composition containing an antibody according to the invention with a pharmaceutically effective amount, optionally together with a buffer and/or an adjuvant useful for the formulation of antibodies for pharmaceutical purposes.

The invention further provides pharmaceutical compositions comprising such antibodies in a pharmaceutically acceptable carrier. In one embodiment, the pharmaceutical composition may be included in an article of manufacture or kit.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or *E. coli* cells, and the antibody is recovered from the cells (supernatant or cells after lysis).

Recombinant production of antibodies is well-known in the state of the art and described, for example, in the review articles of Makrides, S. C., *Protein Expr. Purif.* 17 (1999) 183-202; Geisse, S., et al., *Protein Expr. Purif.* 8 (1996) 271-282; Kaufman, R. J., *Mol. Biotechnol.* 16 (2000) 151-61; Werner, R. G., et al., *Arzneimittelforschung* 48 (1998) 870-80.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NS0 cells is described by, e.g., Barnes, L. M., et al., *Cytotechnology* 32 (2000) 109-123; and Barnes, L. M., et al., *Biotech. Bioeng.* 73 (2001) 261-270. Transient expression is described by, e.g., Durocher, Y., et al., *Nucl. Acids. Res.* 30 (2002) E9. Cloning of variable domains is described by Orlandi, R., et al., *Proc. Natl. Acad. Sci. USA* 86 (1989) 3833-3837; Carter, P., et al., *Proc. Natl. Acad. Sci. USA* 89 (1992) 4285-4289; and Norderhaug, L., et al., *J. Immunol. Methods* 204 (1997) 77-87. A preferred transient expression system (HEK 293) is described by Schlaeger, E.-J., and Christensen, K., in *Cytotechnology* 30 (1999) 71-83 and by Schlaeger, E.-J., in *J. Immunol. Methods* 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of a human OX40L antibody are prepared by introducing appropriate nucleotide changes into the antibody DNA, or by nucleotide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability or facilitate the purification.

Any cysteine residue not involved in maintaining the proper conformation of the anti-OX40L antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Nucleic acid molecules encoding amino acid sequence variants of anti-OX40L antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-OX40L antibody.

The invention also pertains to immunoconjugates comprising the antibody according to the invention conjugated to a cytotoxic agent such as a chemotherapeutic agent, toxin (e.g., an enzymatically active toxin of bacterial, fungal, plant or animal origin, or fragments thereof), a radioactive isotope (i.e., a radioconjugate). Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters; (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediatnine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta, E. S., et al., *Science* 238 (1987) 1098-1104). Carbon-14-labeled 1-isothiocyanatobenzl-3-methyldiethylene triaminepentaacetic acid (MX-DTPA) is an exemplary chelating agent for conjugation of radionucleotide to the antibody. See WO 94/11026.

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

In yet another aspect, the invention provides isolated B-cells from a transgenic non-human animal, e.g. a transgenic mouse, which express the human anti-OX40L antibodies (e.g. the parent antibodies produced by a cell line selected from the group consisting of hybridoma cells producing antibodies according to the invention. Preferably, the isolated B cells are obtained from a transgenic non-human animal, e.g., a transgenic mouse, which has been immunized with a purified or recombinant form of OX40L antigen and/or cells expressing OX40L. Preferably, the transgenic non-human animal, e.g. a transgenic mouse, has a genome comprising a human heavy chain transgene and a human light chain transgene encoding all or a portion of an antibody of the invention. The isolated B-cells are then immortalized to provide a source (e.g. a hybridoma) of human anti-OX40L antibodies. Accordingly, the present invention also provides a hybridoma capable of producing human monoclonal antibodies according to the invention. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell.

In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of OX40L antigen and/or cells expressing OX40L. Preferably, the transgenic non-human animal, e.g. the transgenic mouse, is capable of producing isotypes of human monoclonal antibodies to OX40L.

The human monoclonal antibodies according to the invention can be produced by immunizing a transgenic non-human animal, e.g. a transgenic mouse, having a genome comprising a human heavy chain transgene and a human light chain transgene encoding all or a portion of an antibody of the invention, with a purified or enriched preparation of OX40L antigen and/or cells expressing OX40L. B cells (e.g. splenic B cells) of the animal are then obtained and fused with myeloma cells to form immortal, hybridoma cells that secrete human monoclonal antibodies against OX40L.

In a preferred embodiment, human monoclonal antibodies directed against OX40L can be generated using transgenic mice carrying parts of the human immune system rather than the mouse system. These transgenic mice, referred to herein as "HuMAb" mice, contain a human immunoglobulin gene miniloci that encodes unrearranged human immunoglobulin genes which include the heavy (μ and γ) and κ light chain (constant region genes), together with targeted mutations that inactivate the endogenous, and K chain loci (Lonberg, N., et al., Nature 368 (1994) 856-859). Accordingly, the mice exhibit reduced expression of mouse IgM or K, and in response to immunization, the introduced human heavy and light chain transgenes undergo class switching and somatic mutation to generate high affinity human IgG monoclonal antibodies (Lonberg, N., et al., Nature 368 (1994) 856-859; reviewed in Lonberg, N., Handbook of Experimental Pharmacology 113 (1994) 49-101; Lonberg, N., and Huszar, D., Intern. Rev. Immunol. 25 (1995) 65-93; and Harding, F., and Lonberg, N., Ann. N. Acad. Sci. 764 (1995) 536-546). The preparation of HuMAb mice is described in Taylor, L., et al., Nucleic Acids Res. 20 (1992) 6287-6295; Chen, J., et al., Int. Immunol. 5 (1993) 647-656; Tuaillon, N., et al., Proc. Natl. Acad. Sci. USA 90 (1993) 3720-3724; Choi, T. K., et al., Nat. Genet. 4 (1993) 117-123; Chen, J., et al., EMBO J. 12 (1993) 821-830; Tuaillon, N., et al., J. Immunol. 152 (1994) 2912-2920; Lonberg, N., et al., Nature 368 (1994) 856-859; Lonberg, N., Handbook of Experimental Pharmacology 113 (1994) 49-101; Taylor, L., et al., Int. Immunol. 6 (1994) 579-591; Lonberg, N., and Huszar, D., Intern. Rev. Immunol. 25 (1995) 65-93; Harding, F., and Lonberg, N., Ann. N. Acad. Sci. 764 (1995) 536-546; Fishwild, D. M., et al., Nat. Biotechnol. 14 (1996) 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,545,807; 5,770,429; WO 98/24884; WO 94/25585; WO 93/1227; WO 92/22645; and WO 92/03918.

To generate fully human monoclonal antibodies to OX40L, HuMAb mice can be immunized with a purified or enriched preparation of OX40L antigen and/or cells expressing OX40L in accordance with the general method, as described by Lonberg, N., et al., Nature 368 (1994) 856-859; Fishwild, D. M., et al., Nat. Biotechnol. 14 (1996) 845-851 and WO 98/24884. Preferably, the mice will be 6-16 weeks of age upon the first immunization. For example, a purified or enriched preparation of soluble OX40L antigen (e.g. purified from OX40L-expressing cells) coupled to KLH or in PBS can be used to immunize the HuMAb mice intraperitoneally. This can be combined by alternate immunization with the isolated OX40L protein with cells expressing OX40L, e.g., a tumor cell line, to promote immune responses. Cumulative experience with various antigens has shown that the HuMAb transgenic mice respond best when initially immunized intraperitoneally (i.p.) with antigen in complete Freund's adjuvant, followed by every other week i.p. immunizations (for example, up to a total of 6) with antigen in incomplete Freund's adjuvant. The immune response can be monitored over the course of the immunization protocol with plasma samples being obtained by retroorbital bleeds. The plasma can be screened by ELISA, and mice with sufficient titers of anti-OX40L human immunoglobulin can be used for immortalization of corresponding B cells. Mice can be boosted intravenously with antigen 3 to 4 days before sacrifice and removal of the spleen and lymph nodes. Several mice will be immunized for each antigen. For example, a total of twelve HuMAb mice of the HCo7 and HCo12 strains can be immunized.

The HCo7 mice have a JKD disruption in their endogenous light chain (kappa) genes (as described in Chen, J., et al., EMBO J. 12 (1993) 821-830), a CMD disruption in their endogenous heavy chain genes (as described in Example 1 of WO 01/14424), a KCo5 human kappa light chain transgene (as described in Fishwild, D. M., et al., Nat. Biotechnol. 14 (1996) 845-851), and a HCo7 human heavy chain transgene (as described in U.S. Pat. No. 5,770,429).

The HCo12 mice have a JKD disruption in their endogenous light chain (kappa) genes (as described in Chen, J., et al., EMBO J. 12 (1993) 821-830), a CMD disruption in their endogenous heavy chain genes (as described in Example 1 of WO 01/14424), a KCo5 human kappa light chain transgene (as described in Fishwild, D. M., et al., Nat. Biotechnol. 14 (1996) 845-851), and a HCo12 human heavy chain transgene (as described in Example 2 of WO 01/14424). The mouse lymphocytes can be isolated and fused with a mouse myeloma cell line using PEG based on standard protocols to generate hybridomas. The resulting hybridomas are then screened for the production of antigen-specific antibodies. For example, single cell suspensions of splenic and lymph node-derived lymphocytes from immunized mice are fused to one-sixth the number of SP 2/0 nonsecreting mouse myeloma cells (ATCC, CRL 1581) with 50% PEG. Cells are plated at approximately $2 \times 10^5$ in flat bottom microtiter plate, followed by about two weeks incubation in selective medium.

Individual wells are then screened by ELISA for human anti-OX40L monoclonal IgM and IgG antibodies. Once extensive hybridoma growth occurs, medium is analyzed, usually after 10-14 days. The antibody secreting hybridomas are replated, screened again, and if still positive for human IgG, anti-OX40L monoclonal antibodies, can be subcloned at least twice by limiting dilution. The stable subclones are then cultured in vitro to produce antibody in tissue culture medium for characterization.

The assay tree principally is composed of an unspecific assay on IgG ("IgG-ELISA") followed by a specific ELISA and apparent FACS assay for determination of antigen binding to either purified OX40L protein or OX40L-expressing cells. The next step comprises functional assays where the competition of the anti OX40L antibody with its natural interaction partner e.g. soluble, purified OX40 for either purified OX40L or OX40L expressed on cells is determined, e.g. competition ELISA or FACS. The next step comprises a functional assay where the blocking capability of anti-OX40L antibody of OX40-signal transduction is determined, e.g. NFκB-activation (="NFκB-assay"). The next step comprises functional assays where the blocking capability of the anti-OX40L antibody concerning T-cell activation is determined ("T-cell activation assay" and "TT-assay").

Because CDR sequences are responsible for antibody-antigen interactions, it is possible to express recombinant antibodies according to the invention by constructing expression vectors that include the CDR sequences according to the invention onto framework sequences from a different human antibody (see, e.g., Riechmann, L., et al., Nature 332 (1998) 323-327; Jones, P., et al., Nature 321 (1986) 522-525; and Queen, C., et al., Proc. Natl. Acad. Sci. USA 86 (1989) 10029-10033). Such framework sequences can be obtained from public DNA databases that include germline human antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region.

The invention further comprises the use of an antibody according to the invention for the diagnosis of OX40L in vitro, preferably by an immunological assay determining the binding between OX40L (either soluble or membran-bound) of a sample and the antibody according to the invention.

In another aspect, the present invention provides a composition, e.g. a pharmaceutical composition, containing one or a combination of human monoclonal antibodies, or the antigen-binding portion thereof, of the present invention, formulated together with a pharmaceutically acceptable carrier. More specifically, the composition is a pharmaceutical or a diagnostic composition and even more specifically the pharmaceutical composition comprises an antibody as defined above and at least one pharmaceutically acceptable excipient. The composition must be sterile and fluid to the extent that the composition is deliverable by syringe.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). Preferably such a carrier is an aqueous pH buffered solution (for example acetate, citrate, phosphate or histidine), preferably isotonic, preferably containing in addition an inorganic salt, sugar, polyol and/or a surfactant. Pharmacaeutical acceptable carriers are also such as described in *Remington's Pharmaceutical Sciences,* 16$^{th}$ edition, Osol, A. Ed. (1980).

The antibody concentration is preferably from 0.1 mg/ml to 50 mg/ml. Preferably the pH value of the buffered solution ranges from 4.0 to 8.0 at a buffer concentration of 1 mM to 200 mM. Preferred salts are sodium chloride and/or sodium phosphate in the range of 1 mM to 200 mM. Preferred sugars are sucrose and/or trehalose in the range of 1% to 15% (w/v). Preferred polyols are glycerol, propylene glycol, liquid polyetheylene glycol, and/or the like in the range of 1% to 15% (w/v). The surfactant is preferably a polysorbate (e.g. polysorbate 20 or 80) and/or poloxamere in the range of 0.001% to 0.5% (w/v). A preferred pharmaceutical composition contains antibody from 0.1 mg/ml to 50 mg/ml and 1 mM to 200 mM phosphate buffered saline pH 4.0 to 8.0.

A composition of the present invention can be administered by a variety of methods known in the art to a patient with the need thereof. As will be appreciated by the skilled artisan, the route and/or mode of administration will vary depending upon the desired results.

Pharmaceutically acceptable excipients or carriers include sterile aqueous solutions or sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A typical weekly dosage might range from about 0.1 mg/kg to about 20 mg/kg or more, depending on the factors mentioned above.

The following examples, references, sequence listing and figures are provided to aid the understanding of the present invention, the true scope of which is set forth in the appended claims. It is understood that modifications can be made in the procedures set forth without departing from the spirit of the invention.

Abbreviations:

Amino acids are abbreviated either in the three (Leu) or one letter code (L). S228P means an exchange of Serin to Proline at position 228 of IgG4 heavy chain. L234 means amino acid leucine at position 234 according to EU numbering (Kabat). L234A means amino acid leucine at position 234 is changed to alanine. L235A means amino acid leucine at position 235 is changed to alanine. PVA236 means that in the 236 region ELLG of IgG1 or EFLG of IgG4 is amended in PVA. GLPSS331 means that in the 331 region ALPAP of IgG1 or GLPAP of IgG2 is changed to GLPSS. Delta G236 means amino acid at position 236 is deleted. IgG4x means mutation S228P in IgG4. LC2010-001 is a synonym for LC.001 Fcg is synonymous for Fcgamma (Fcγ)

Other sequence amendments of antibodies are designated analogously.

| | |
|---|---|
| Recombinant soluble human OX40L fused to a Histidine tag | hOX40L-His |
| Recombinant soluble murine OX40L fused to a Histidine tag | mOX40L-His |
| Recombinant soluble human OX40L fused to a Flag tag | hOX40L-Flag |
| Recombinant soluble murine OX40L fused to a Flag tag | mOX40L-Flag |
| Recombinant soluble human OX40 fused to human Fcγ | hOX40-hFc |
| Rabbit anti-murine Fcγ monoclonal antibody | Anti-mFc |
| Goat anti-human Fcγ monoclonal antibody | Anti-hFc |
| Murine anti-histidine monoclonal antibody | Anti-His |
| Recombinant soluble human OX40 fused to murine Fcγ | hOX40-mFc |
| Murine anti-TNFα monoclonal antibody | Anti-TNFα |
| Murine anti-CD40L monoclonal antibody | Anti-CD40L |
| Tumor Necrosis Factor alpha | TNFα |
| CD40 Ligand | CD40L |
| Rat anti-human OX40L monoclonal antibody | TAG34 |
| Human anti-human OX40L monoclonal antibody | LC.001 |

| | |
|---|---|
| Human anti-human OX40L monoclonal antibody | LC.005 |
| Human anti-human OX40L monoclonal antibody | LC.010 |
| Human anti-human OX40L monoclonal antibody | LC.019 |
| Human anti-human OX40L monoclonal antibody | LC.029 |
| Human anti-human OX40L monoclonal antibody | LC.033 |
| phytohemagglutinin | PHA |

EXAMPLES

Example 1

Generation of a Hybridoma Cell Line Producing Anti-OX40L Antibodies

Culture of hybridomas: HuMab hybridomas were cultured in IMDM (Cambrex), Fetal clone 1 Bovine serum (Perbio Science), origin Hybridoma cloning factor (Igen), sodium pyruvate, penicillin/streptomycin, 2-mercaptoethanol, HAT (Sigma-Aldrich) and Kanamycin (Invitrogen) in 37° C. and 5% $CO_2$.

Immunization procedure of transgenic mice: LC2010-001: Six HCo7 (2 males and 4 females), strain GG2201 (Medarex, San Jose, Calif., USA), and 4 HCo12 (4 males), strain GG2198 (Medarex, San Jose, Calif., USA) were alternatingly immunized with $1 \times 10^6$ HEK293 cells, transiently transfected with an expression vector for human OX40L (hOX40L), and 20 µg soluble extracellular domain of hOX40L. Eight immunizations were performed in total, four intraperitoneal (i.p.) immunizations with the hOX40L expressing cells and four subcutaneous (s.c.) immunizations at the tail base with recombinant protein. For the first immunization, 100 µl of $1 \times 10^6$ HEK293-hOX40L cells was mixed with 100 µl complete Freund's adjuvant (CFA; Difco Laboratories, Detroit, USA). For all other immunizations, 100 µl of cells in PBS were used or recombinant protein was mixed with 100 µl incomplete Freund's adjuvant (ICFA; Difco).

When serum titers of anti-hOX40L were found to be sufficient, mice were additionally boosted twice with 15 µg hOX40L extracellular domain in 200 µl PBS intravenously (i.v.) 4 and 3 days before fusion. LC2010-001 was derived from one of the HCo12 mice.

LC2010-005, -010, -019, -029 and -033: Five HCo7 (4 males and 1 female), strain GG2201 (Medarex, San José, Calif., USA) were immunized with 20 µg soluble extracellular domain of hOX40L. Seven immunizations were performed in total, four intraperitoneal (i.p.) and three subcutaneous (s.c.) immunizations at the tail base. For the first immunization, 100 µl of recombinant protein was mixed with 100 µl complete Freunds' adjuvant (CFA; Difco Laboratories, Detroit, USA). For all other immunizations, 100 µl of recombinant protein was mixed with 100 µl incomplete Freunds' adjuvant (ICFA; Difco).

When serum titers of anti-hOX40L were found to be sufficient, mice were additionally boosted twice with 15 µg hOX40L extracellular domain in 200 µl PBS intravenously (i.v.) 4 and 3 days before fusion.

Hybridoma generation: Mice were sacrificed and the spleen and lymph nodes flanking the abdominal aorta and vena cava were collected. Fusion of splenocytes and lymph node cells with the fusion partner SP 2.0 cells was performed according to standard operating procedures.

Antigen specific ELISA: Anti-OX40L titers in sera of immunized mice were determined by antigen specific ELISA. Plate (96 flat bottom ELISA plate, Greiner) was coated with 0.1 µg/ml purified OX40L dissolved in PBS and coated overnight at room temperature. Thereafter, wells were blocked with PBSTC (PBS containing 0.05% Tween 20 (Sigma-Aldrich Chemie BV) and 2% chicken serum (Gibco)) for 1 hour at room temperature.

Tested serum taps were diluted 1:50 in PBSTC and added to the wells. Serum obtained from mice prior to immunization was dissolved 1:100 in PBSTC and used as negative control. A mouse antibody directed against human OX40L was dissolved 1:50 in PBSTC and used as a positive control. Plates were incubated for 1 hour at room temperature. Subsequently, plates were washed twice using PBST (PBS containing 0.05% Tween 20. Gt-α-huIgG-HRP (Jackson) was diluted 1:5000 in PBSTC and added to the wells containing the tested taps and the negative control. Rb-α-mIgG (Jackson) was diluted 1:3000 in PBSTC and added to the wells containing the positive control. Plates were incubated for 1 hour at room temperature. Finally, plates were washed three times using PBST and developed with freshly prepared ABTS® solution (1 mg/ml) (ABTS: 2,2'-azino bis(3-ethyl-benzthiazoline-6-sulfonic acid) for 30 minutes at room temperature (RT) in the dark. Absorbance was measured at 405 nm.

kappa-ELISA: To determine whether hybridomas that resulted from the fusion generate human antibodies, a kappa-ELISA was performed. ELISA plates were coated with rat anti-human IgG kappa-light chain antibody (DAKO) diluted 1/10000 in PBS by overnight incubation at 4° C. After discarding the wells, plates were blocked by incubation with PBSTC (PBSC, supplemented with 0.05% Tween-20 (PBSTC)) for 1 hour at room temperature. Thereafter, wells were incubated with hybridoma culture supernatant, 1/2 diluted in PBSTC. Culture medium 1/2 diluted in PBSTC was used as negative control, kappa-light positive mouse serum 1/100 diluted in PBSTC served as positive control. Subsequently, wells were washed thrice and were incubated with HRP-conjugated rat anti-human IgG F(ab')$_2$ (DAKO), diluted 1/2000 in PBSTC for 1 h at 37° C. Wells were washed thrice and assays were developed with freshly prepared ABTS® solution (1 mg/ml) for 30 minutes at room temperature (RT) in the dark. Absorbance was measured at 405 nm in an ELISA plate reader.

Example 2

Cloning and Sequence Analysis of Anti-OX40L HuMab Variable Domains kappa-light and γ1-heavy chains: The nucleotide sequences coding for the light chain variable region $V_L$ and the heavy chain variable region $V_H$ of the OX40L HuMabs were isolated by a standard cDNA synthesis/PCR procedure.

Total RNA was prepared from $1 \times 10^6$-$1 \times 10^7$ hybridoma cells using the GeneRacer™ Kit (Invitrogen). Hybridoma derived RNA was used as a template for the $1^{st}$ strand cDNA synthesis and ligation of the GeneRacer™ Oligo-dT Primer. $2^{nd}$-strand cDNA synthesis and further PCR amplification of $V_L$ and $V_H$ encoding cDNA fragments were performed with revers light and heavy chain primers complementary to nucleotide sequences of the kappa-light and γ1-heavy chain constant region and 5'-specific GeneRacemm primers, respectively. The PCR products were cloned using the TOPO™ TA cloning kit from Invitrogen™ Life Technologies and pCR4-

TOPO™ as a cloning vector. Cloned PCR products were identified by restriction mapping of the appropriate plasmids using EcoRI for digestion and expected/calculated DNA fragment sizes of about 740 and 790 bp for $V_L$ and $V_H$, respectively.

The DNA sequence of cloned PCR fragments was determined by double strand sequencing.

The GCG (Genetics Computer Group, Madison, Wis.) software package version 10.2 and Vector-NTI 8 (InforMax, Inc) was used for general data processing. DNA and protein sequences were aligned using the GCG module CLUSTALW. Sequence alignments were made using the program GENE-DOC (version 2.1).

Example 3

Construction of Expression Plasmids for an Anti-OX40L IgG1 HuMab

The anti-OX40L HuMab light and heavy chain encoding genes were separately assembled in mammalian cell expression vectors.

Thereby the gene segments encoding the anti-OX40L HuMab light chain variable region ($V_L$) and the human kappa-light chain constant region ($C_L$, SEQ ID NO:13) were joined as were gene segments for the anti-OX40L HuMab heavy chain variable region ($V_H$) and the human γ1-heavy chain constant region ($C_{H1}$-Hinge-$C_{H2}$—$C_{H3}$, SEQ ID NO:14).

General information regarding the nucleotide sequences of human light and heavy chains from which the codon usage can be deduced is given in: Kabat, E. A., et al., *Sequences of Proteins of Immunological Interest*, fifth ed., NIH Publication No. 91-3242 (1991).

The transcription unit of the anti-OX40L HuMab kappa-light chain is composed of the following elements:
The immediate early enhancer and promoter from the human cytomegalovirus (HCMV),
A synthetic 5'-UT including a Kozak sequence,
A murine immunoglobulin heavy chain signal sequence including the signal sequence intron,
The cloned anti-OX40L HuMab variable light chain cDNA arranged with a unique BsmI restriction site at the 5' end and a splice donor site and a unique NotI restriction site at the 3' end,
The genomic human kappa-gene constant region, including the intron 2 mouse Ig-kappa enhancer (Picard, D., and Schafffier, W., *Nature* 307 (1984) 80-82) and
The human immunoglobulin kappa-polyadenylation ("poly A") signal sequence.

The transcription unit of the anti-OX40L HuMab γ1-heavy chain is composed of the following elements:
The immediate early enhancer and promoter from the human cytomegalovirus (HCMV),
A synthetic 5'-UT including a Kozak sequence,
A modified murine immunoglobulin heavy chain signal sequence including the signal sequence intron,
The cloned anti-OX40L HuMab variable heavy chain cDNA arranged with a unique BsmI restriction site at the 5' and a splice donor site and a unique NotI restriction site at the 3' end,
The genomic human γ1-heavy gene constant region, including the mouse Ig μ-enhancer (Neuberger, M. S., *EMBO J.* 2 (1983) 1373-1378),
The human γ1-immunoglobulin polyadenylation ("poly A") signal sequence.

Functional elements of the anti-OX40L HuMab kappa-light chain and γ1-heavy chain expression plasmids: Beside the anti-OX40L HuMab kappa-light chain or γ1-heavy chain expression cassette these plasmids contain
A hygromycin resistance gene
An origin of replication, oriP, of Epstein-Barr virus (EBV)
An origin of replication from the vector pUC18 which allows replication of this plasmid in *E. coli*, and
A Δ-lactamase gene which confers ampicillin resistance in *E. coli*.

Example 4

Construction of Expression Plasmids for an Anti-OX40L IgG4 HuMab

An anti-OX40L γ4-heavy chain prototype expression plasmid was derived from the anti-OX40L γ1-heavy chain expression plasmid by replacing the human genomic γ1-constant region and γ1-immunoglobulin polyadenylation ("poly A") signal sequence by the human genomic γ4-constant region (SEQ ID NO:15) and γ4-immunoglobulin polyadenylation-signal sequence.

For the expression of anti-OX40L HuMab kappa-light chains the same expression plasmids were used as described for IgG1 (see above).

Example 5

Construction of Expression Plasmids for Mutant (Variant) Anti-OX40L IgG1 and IgG4 Based on LC.001

Expression plasmids encoding mutant anti-OX40L γ1- and γ4-heavy chains were created by site-directed mutagenesis of the wild type expression plasmids using the QuickChange™ Site-Directed mutagenesis Kit (Stratagene). Amino acids are numbered according to EU numbering (Edelman, G. M., et al., *Proc. Natl. Acad. Sci. USA* 63 (1969) 78-85; Kabat, E. A., et al., Sequences of Proteins of Immunological Interest, 5th ed., Public Health Service, NIH Publication No. 91-3242, Bethesda, Md. (1991)).

TABLE 1

| Isotype | Abbreviation | Mutations | Description |
|---|---|---|---|
| IgG1 | IgG1v1 | PVA-236; GLPSS331 as specified by E233P; L234V; L235A; delta G236; A327G; A330S; P331S | The amino acid sequence $Glu_{233}Leu_{234}Leu_{235}Gly_{236}$ of the human γ1-heavy chain is replaced by the amino acid sequence $Pro_{233}Val_{234}Ala_{235}$ of the human γ2-heavy chain. The amino acid sequence $Ala_{327}Leu_{328}Pro_{329}Ala_{330}Pro_{331}$ of the human γ1-heavy chain is replaced by the amino acid sequence $Gly_{327}Leu_{328}Pro_{329}Ser_{330}Ser_{331}$ of the human γ4-heavy chain. |
| IgG1 | IgG1v2 | L234A; L235A | The amino acid sequence $Leu_{234}Leu_{235}$ of the human γ1-heavy chain is replaced by the amino acid sequence $Ala_{234}Ala_{235}$ |

TABLE 1-continued

| Isotype | Abbreviation | Mutations | Description |
|---------|--------------|-----------|-------------|
| IgG4 | IgG4v1 | S228P; L235E | $Ser_{228}$ of the human γ4-heavy chain is replaced by $Pro_{228}$ and $Leu_{235}$ of the human γ4-heavy chain is replaced by $Glu_{235}$ |
| IgG4 | IgG4x | S228P | $Ser_{228}$ of the human γ4-heavy chain is replaced by $Pro_{228}$ |

Example 6

Production of Recombinant Anti OX40L HuMabs

Recombinant HuMabs were generated by transient transfection of adherent HEK293-EBNA cells (ATTC CRL-10852) cultivated in DMEM (Gibco) supplemented with 10% ultra-low IgG FCS (Gibco), 2 mM Glutamine (Gibco), 1% v/v nonessential aminoacids (Gibco) and 250 μg/ml G418 (Roche). For transfection Fugene™ 6 (Roche) Transfection Reagent was used in a ratio of reagent (μl) to DNA (μg) ranging from 3:1 to 6:1. Immunoglobulin light and heavy chains were expressed from two different plasmids using a molar ratio of light chain to heavy chain encoding plasmid from 1:2 to 2:1. HuMab containing cell culture supernatants were harvested at day 4 to II after transfection. Supernatants were stored at −20° C. until purification.

General information regarding the recombinant expression of human antibody in e.g. HEK293 is given in: Meissner, P., et al., *Biotechnol. Bioeng.* 75 (2001) 197-203.

Example 7

Affinity Analysis of Antibodies TAG34, LC.001, LC.005, LC.010, LC.019, LC.029, LC.033

Instrument: Biacore 3000, running and reaction buffer: HBS-P (10 mM HEPES, 150 mM NaCl, 0.005% Tween 20, ph 7.4), 25° C. Injection of analyte was performed at 7 concentrations between 0.78 nM and 100 nM for 3 minutes and washed with HBS-P for 5 minutes. Regeneration of the surface (carboxymethylated dextrane surface, CM) was performed by two injections of 10 mM Glycine pH 2.0 for 1 min each. The chip, assay format and sequence of injections and kinetic data correspond to the description in the following table. Kinetic data were calculated by fitting kinetic data to a 1:1 Langmuir binding model.

Data Evaluation and Data Deposition for all Biacore assays: Negative control data (e.g. buffer curves) were subtracted from sample curves for correction of system intrinsic baseline drift and for noise signal reduction. BiaEvaluation version 4.01 was used for analysis of sensorgrams and for calculation of affinity data.

Example 8

Inhibitory Competition Assay of Anti-hOX40L Antibodies Inhibiting the Interaction of hOX40L with Immobilized hOX40

Instrument: Biacore 3000, running and reaction buffer: HBS-P (10 mM HEPES, 150 mM NaCl, 0.005% Tween 20, ph 7.4), 25° C. Prior to injection the analyte (10 nM) and competitor (eight concentrations between 0.78 nM and 100 nM) were preincubated for at least 20 min at 22° C. Injection of analyte+/−competitor was performed for 3 minutes and washed with HBS-P for three minutes. Regeneration of the surface was performed by two injections of 10 mM Glycine pH 2.0 for 1 min each. The chip, assay format and sequence of injections and kinetic data correspond to the description in the following table 3.

TABLE 3

| Chip | Ligand | Analyte | Competitor | IC50 (M) |
|------|--------|---------|------------|----------|
| CM5 | OX40-hFc | hOX40L-His | TAG34 | $7 \times 10^{-9}$ |
| CM5 | OX40-hFc | hOX40L-His | LC.001 | $4 \times 10^{-9}$ |
| CM5 | OX40-hFc | hOX40L-His | LC.005 | $3 \times 10^{-9}$ |

All antibodies inhibit the binding of OX40L to OX40 in solution (solution affinity). LC.001 and LC.005 show a lower IC50-value than TAG34.

Example 9

Epitope Characterization of Anti-OX40L Antibodies TAG34, LC.001, LC.005, LC.010, LC.019, LC.029, LC.033

Instrument: Biacore 3000, running and reaction buffer: HBS-P (10 mM HEPES, 150 mM NaCl, 0.005% Tween 20, ph 7.4), 25° C. The epitope groups were determined by cross competition between the listed antibodies. Prior to injection the analyte (50 nM) and competitor (100 nM) were preincubated for at least 20 min at 22° C. Injection of analyte+/−competitor for two minutes, wash with HBS-P for three minutes. Regeneration of the surface was performed by two injections of 10 mM Glycine pH 2.0 for 1 min each. The chip,

TABLE 2

| Chip | Capturing | Ligand | Analyte | ka (1/Ms) | kd (1/s) | $K_D$ (M) |
|------|-----------|--------|---------|-----------|----------|-----------|
| CM5 | Anti-mFcg | TAG34 | hOX40L-His | $8.84 \times 10^4$ | $3.32 \times 10^{-5}$ | $3.75 \times 10^{-10}$ |
| CM5 | Anti-hFcg | LC.001 | hOX40L-His | $9.01 \times 10^4$ | $7.16 \times 10^{-9}$ | $<1.1 \times 10^{-11}$ |
| CM5 | Anti-hFcg | LC.005 | hOX40L-His | $6.84 \times 10^4$ | $2.02 \times 10^{-7}$ | $<1.5 \times 10^{-11}$ |
| CM5 | Anti-hFcg | LC.010 | hOX40L-His | $6.25 \times 10^4$ | $2.5 \times 10^{-5}$ | $3.99 \times 10^{-10}$ |
| CM5 | Anti-hFcg | LC.019 | hOX40L-His | $7.89 \times 10^4$ | $7.53 \times 10^{-8}$ | $<1.2 \times 10^{-11}$ |
| CM5 | Anti-hFcg | LC.029 | hOX40L-His | $1.41 \times 10^5$ | $2.4 \times 10^{-8}$ | $<7.1 \times 10^{-12}$ |
| CM5 | Anti-hFcg | LC.033 | hOX40L-His | $7.01 \times 10^4$ | $2.09 \times 10^{-7}$ | $<1.4 \times 10^{-11}$ |

No interaction between TAG34 and mOX40L could be measured.

assay format and sequence of injections and kinetic data correspond to the description in the following table 4.

TABLE 4

| Chip | Capturing | Ligand | Analyte | Competitor | Epitope |
|---|---|---|---|---|---|
| CM5 | Anti-hFcg | Anti-OX40L (A,B,C) | hOX40L-His | TAG34 | A |
| CM5 | Anti-hFcg | Anti-OX40L (A,B,C) | hOX40L-His | LC.001 | A |
| CM5 | Anti-hFcg | Anti-OX40L (A,B,C) | hOX40L-His | LC.005 | B |
| CM5 | Anti-hFcg | Anti-OX40L (A,B,C) | hOX40L-His | LC.010 | B |
| CM5 | Anti-hFcg | Anti-OX40L (A,B,C) | hOX40L-His | LC.019 | A/B |
| CM5 | Anti-hFcg | Anti-OX40L (A,B,C) | hOX40L-His | LC.029 | B |
| CM5 | Anti-hFCg | Anti-OX40L (A,B,C) | hOX40L-His | LC.033 | A |

The OX40L epitope recognized by TAG34 was defined as epitope A. Antibodies within one epitope group (A or B) show cross inhibitory activity, while antibodies from different groups show additive binding signals. LC.019 neutralizes other antibodies from group A as well as from group B.

Example 10

Binding Specificity of TAG34, LC.001 and LC.005 to CD40L and TNFα

Instrument: Biacore 3000, running and reaction buffer: HBS-P (10 mM HEPES, 150 mM NaCl, 0.005% Tween 20, ph 7.4), 25° C. Injection of analyte was performed for three minutes at 100 nM and 500 nM and washed with HBS-P for two minutes. Regeneration of the surface was performed by two injections of 100 mM HCl for 1 min each. The chip, assay format and sequence of injections and kinetic data correspond to the description in the following table 5.

TABLE 5

| Chip | Capturing | Ligand | Analyte |
|---|---|---|---|
| CM5 | Anti-mFcg<br>Anti-hFcg | TAG34<br>LC.001<br>LC.005<br>Anti-TNFα<br>Anti-CD40L | TNFα<br>CD40L<br>OX40L |

In this assays CD40L showed some unspecific binding to all antibodies or to the chip surface, but after subtraction of background signals this assay showed, that there was no unspecific binding of TNFα and CD40L (up to 500 nM) to the immobilized antibodies TAG34, LC.001 and LC.005.

Example 11

Affinity Analysis of Antibodies LC.001-IgG1 and LC.001-IgG4x

Instrument: Biacore 3000, running and reaction buffer: HBS-P (10 mM HEPES, 150 mM NaCl, 0.005% Tween 20, ph 7.4), 25° C. Injection of analyte was performed at eight concentrations of 0.78 nM-100 nM for three minutes and washed with HBS-P for five minutes. Regeneration of the surface was performed by two injections of 100 mM HCl for 1 min each. The chip, assay format and sequence of injections and kinetic data correspond to the description in the following table. Kinetic data were calculated by fitting kinetic data to a 1:1 Langmuir binding model.

TABLE 6

| Chip | Capturing | Ligand | Analyte | ka (1/Ms) | kd (1/s) | $K_D$ (M) |
|---|---|---|---|---|---|---|
| CM5 | Anti-mFcg | LC.001 | hOX40L-His | $4.27 \times 10^4$ | $3.46 \times 10^{-8}$ | $<2.3 \times 10^{-11}$ |
| CM5 | Anti-mFcg | LC.001-IgG4x | hOX40L-His | $4.85 \times 10^4$ | $7.72 \times 10^{-8}$ | $<2.06 \times 10^{-11}$ |

LC.001 and LC.001-IgG4x show the same affinity to hOX40L-His.

Example 12

ELISA Assay for Detection of Antibodies Binding to OX40L

SA-coated plates (96 flat bottom ELISA plate, Microcoat) were coated with 0.5 µg/ml biotinylated OX40L dissolved in incubation buffer (IB=PBS containing 0.1% Tween 20 (Serva) and 1% blocking protein) for 1 hour at room temperature. Then the plates were washed twice using washing buffer (WB=saline containing 0.1% Tween 20).

Samples (cell culture supernatants or purified antibodies) were serially diluted in IB and added to the wells. Plates were incubated for 1 hour at room temperature. Subsequently, plates were washed twice using WB. Subsequently a conjugate of a goat antibody against human IgG and POD (Dianova) was diluted to 50 ng/ml in IB and added to the wells. Plates were incubated for 1 hour at room temperature. Finally, plates were washed twice using WB and developed with ready-to-use ABTS® solution (Roche) at room temperature (RT) in the dark. Absorbance was measured at 405 nm after absorbance of the highest concentration reached a sufficient OD (FIG. 1a). EC50 values are obtained in the range of 3 nM-8 mM.

Example 13

ELISA Assay for Detection of Antibodies Inhibiting Interaction of Human OX40/Human OX40L SA-coated plates (96 flat bottom ELISA plate, Microcoat, Germany) were coated with 0.5 µg/ml biotinylated OX40L dissolved in IB for 1 hour at room temperature. Then the plates were washed twice using WB (PBS buffer, 0.1% (w/v) Tween™ 20.

Figure 1B:
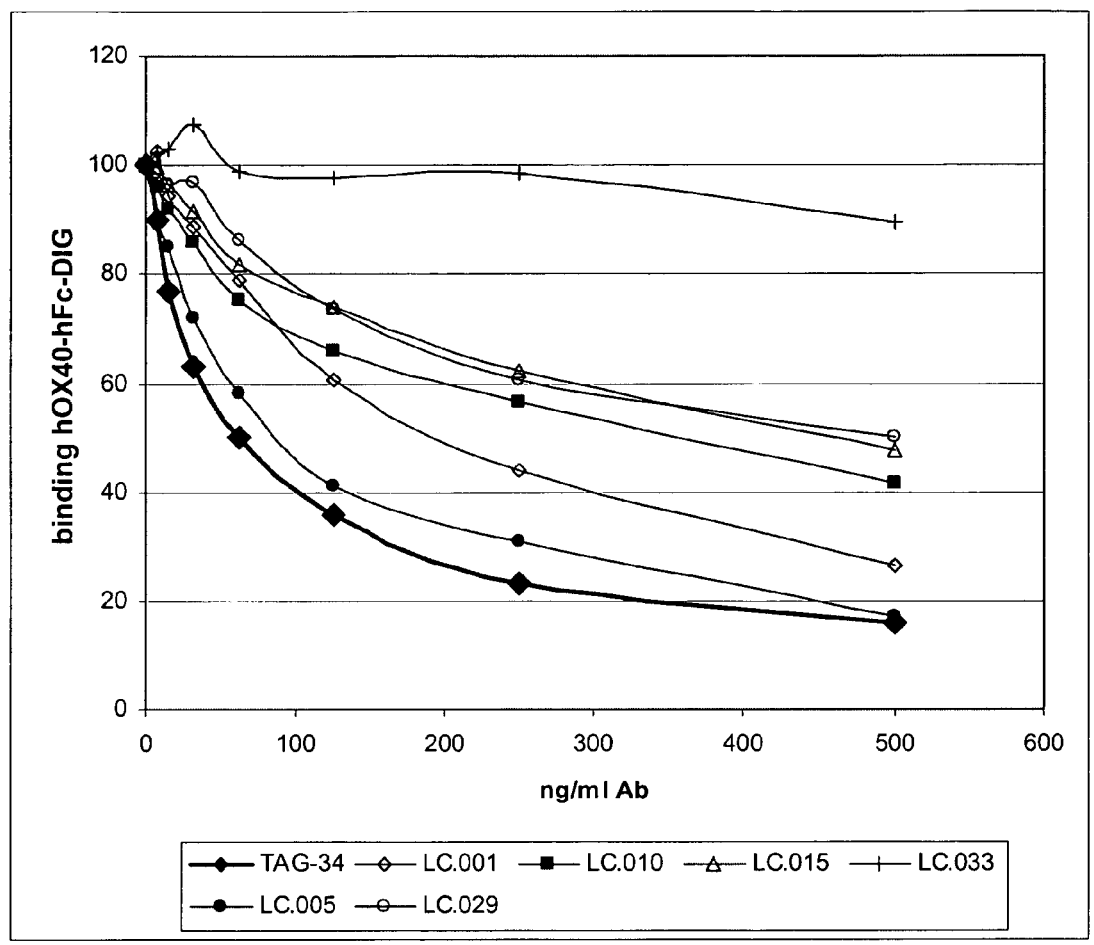
FIG. 1b shows "blocking ELISA"+IC$_{50}$ data for TAG-34, LC.001, LC.005, LC.010, LC.019, LC.029, LC.033.

Samples were diluted in IB to a concentration of 1 µg/ml and added to the wells in serial dilutions. In order to achieve maximum binding of OX40 to OX40L in some well only IB was added. Then to each well a solution of human OX40 conjugated with Digoxigenin (Roche Diagnostics GmbH, DE) at a concentration of 0.2 µg/ml was added. Plates were incubated for 1 hour at room temperature. Subsequently, plates were washed twice using WB. Sheep<Digoxigenin>-POD (Roche) was diluted to 50 mU/ml in IB and added to the wells. Plates were incubated for 1 hour at room temperature. Finally, plates were washed twice using WB and developed with ready-to-use ABTS® solution (Roche) at room temperature (RT) in the dark. Absorbance was measured at 405 run after 10 to 20 minutes (FIG. 1b). IC50 values were obtained in the range between 1 mM and 4 nM.

Example 14

FACS-Assay for Detection of HuMabs Inhibiting Interaction of Human OX40 with Human OX40L Expressed on K562 Cells (K562_OX40L Cells)

Purpose: Assay for determination of the HuMab hOX40L's property to block interaction of Dig-labeled hOX40:hFc fusion protein with hOX40L expressing cell line K562_hOX40L.

Procedure: The assay is performed with Dig labeled hOX40:hFc as "assay reagent" and the HuMab hOX40L as "competitor".

Assay reagent: stock 0.5 µg/µl-1:10 diluted in PBS), 100 µl anti digoxigenin-FLUOS. 1:25 diluted in PBS/0.5% BSA/1% blocking reagent (Roche Diagnostics GmbH, DE).

Figure 2:
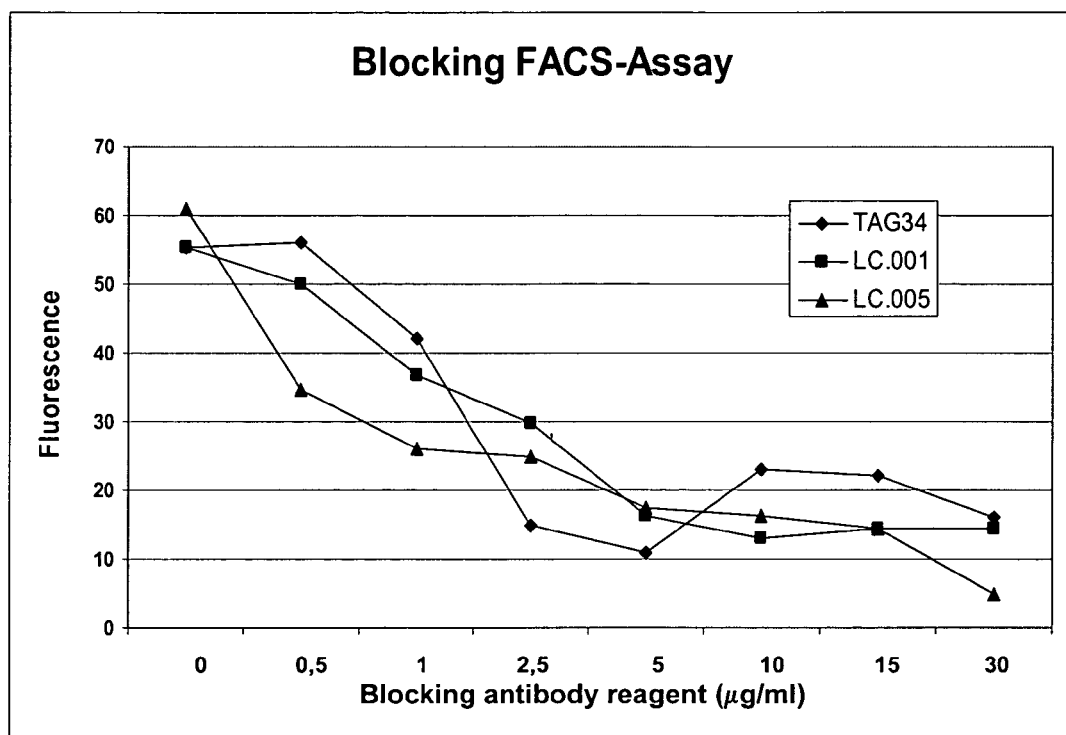
FIG. 2 shows "blocking FACS" for TAG-34, LC.001, LC.005.

$2 \times 10^5$ K562_OX40L cells (grown in ISF-0) were washed in 2 ml PBS and resuspended in 100 µl PBS. This is followed by the addition of competitor in PBS (competitor/reagent relation of 0:1/1:1/1.5:1/2:1/2.5:2/5:1). This is followed by an incubation time of 30 Min, RT and day light. Then reagent (in PBS) was added; incubation time: 30 Min, RT and day light. The cells were washed with 2 ml PBS and pelleted by centrifugation. The secondary antibody for staining (anti-digoxigenin-fluorescein, Fab-Fragments (Roche, 1207741)) was added and incubated for 30 Min, 4° C. in the dark. The cells were washed with 2 ml PBS and pelleted by centrifugation. After that the cells were resuspended in 0.5 ml PBS. Measurement of the samples was performed in a FACS-Scan (FIG. 2).

Example 15

Functional Assay for Determination of the Inhibitory Capacity of Antibodies for hOX40/hOX40L Signaling ("NFκB-Assay")

HeLa wild type (wt) and HeLa cells expressing human OX40 (HeLa_OX40) were grown in Minimal Essential Medium (MEM), 1×Na-pyruvate, 1× Non Essential Aminoacids (Gibco), 10% FCS and in the case of the recombinant cells+600 µg/ml G418. K562 and K562 expressing OX40L were grown in ISF-O medium, and in the case of recombinant cells 200 µg/ml G418 was added.

Figure 3:
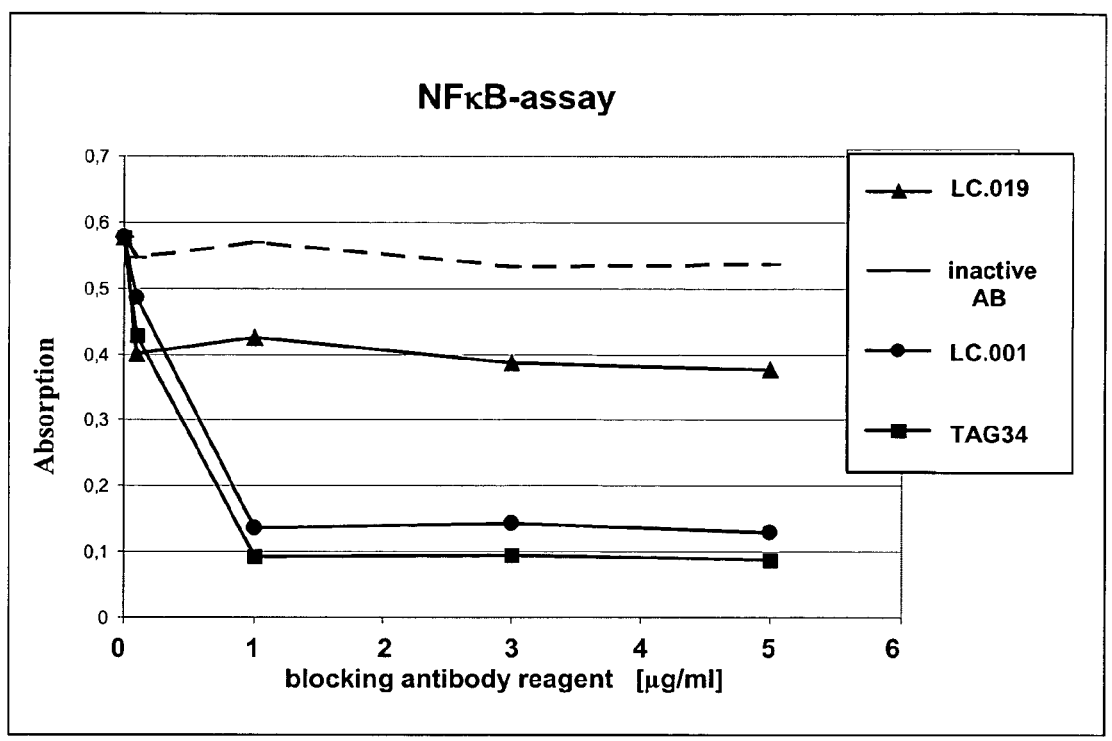
FIG. 3 shows "NFkB-assay" for TAG-34, LC.001, LC.019 and LC.024 (non binding antibody).

HeLa_wt or HeLa_OX40 cells were seeded at a cell density of $3 \times 10^4$ cells/100 µl in a 96-well plate w/o G418 and incubated over night in a $CO_2$-incubator. K562_wt or K562_OX40L cell were added in a cell-to-cell relation of 1:1. Formalin-fixed or not formalin-fixed K562 cells expressing OX40L (frozen at −70° C.) were thawed and diluted 1:10 in MEM/10% FCS; the K562_OX40L cells were preincubated with antibody against OX40L for 30 min at RT. The stimulation time with the K562_OX40L cells was between 30 and 150 min. Protein extraction from cell nuclei took place according suppliers instruction with the NE-Kit from Active Motif. The TransAM NFκB-ELISA from Active Motif (the assay was performed according suppliers instructions) was used to determine OX40-signaling, which results in NFκB activation. The measurement was performed at wavelength 450/620 nm absorption in a Tecan MTP-Reader (FIG. 3). IC50 values were obtained in the range between 1 and 5 nM.

Example 16

T-Cell Activation Assay

Assay principle: Human peripheral blood mononuclear cells (PBL) are activated with a sub-optimal concentration of the T-cell mitogen phyto-hemagglutinin (PHA), and co-stimulated with K562 cells overexpressing OX40L. Under the assay conditions, activated T-cells incubated 24 hr at 37° C. produce IL-2. The cytokine is measured in the supernatant using an ELISA assay. To determine the blocking effect of a Mab, the K562_OX40L cells are pre-incubated for 1 hour with appropriate dilutions of the antibody before co-culture with PBL.

Figure 4:
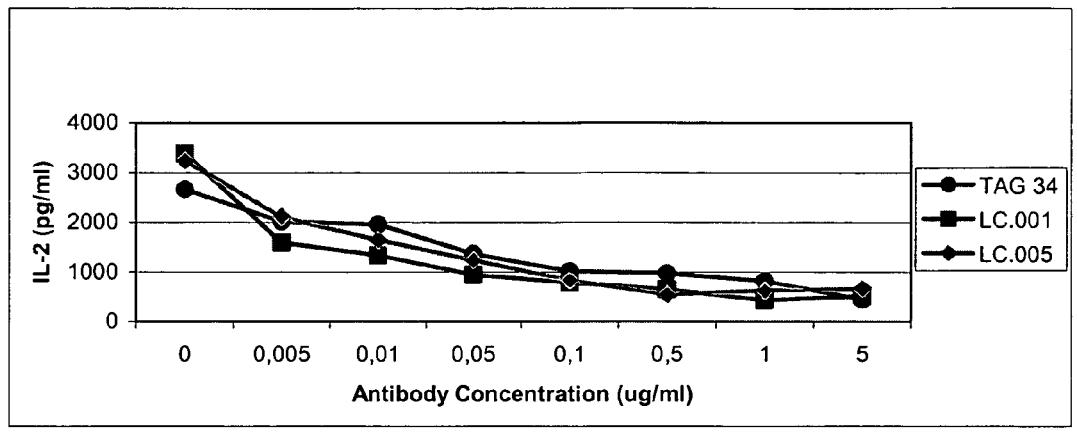
FIGS. 4 and 5 show "T-cell activation assay" and IC50-values for TAG-34, LC.001 and LC.005 (FIG. 4: IL-2 release, FIG. 5: inhibition).
Figure 5:
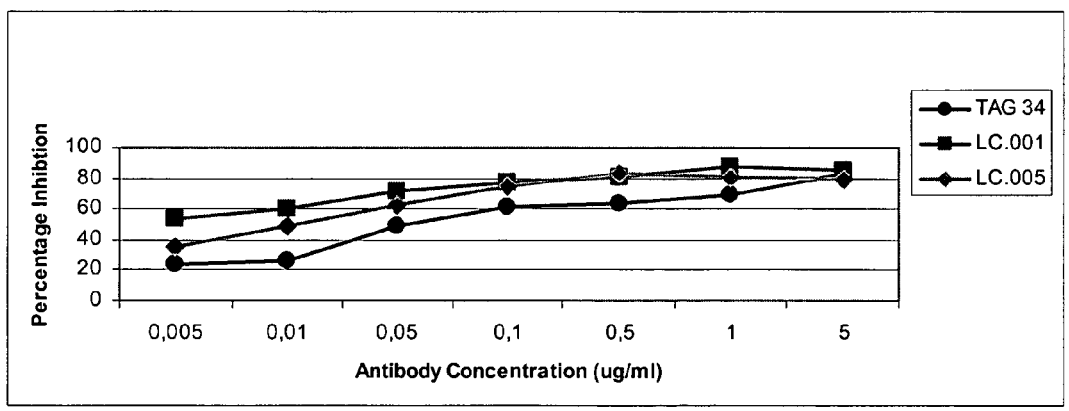

Procedure: Human peripheral blood mononuclear cells (PBL) are separated from heparinized whole blood by density gradient centrifugation in Histopaque®-1077 (Sigma). After washing with Hanks, cells are counted using Turk's solution, and the cell are resuspended at a concentration of $10^6$/ml in RPMI 1640 (Gibco), supplemented with penicillin, streptomycin and glutamine (Gibco 10378-016), and 10% FBS. K562 control cells (wild type) are maintained in the same RPMI medium supplemented as described. K562 cells transfected with OX40L are maintained in the same medium supplemented with Geneticin (G418, Gibco) at a final concentration of 50 mg/ml. K562 cells (either WT or OX40L+) are diluted with the same medium at $1.5 \times 10^5$ cells/ml, and dispensed into each well of a 96 well tissue culture plate at 50 µl/well (0.75×104/well). Appropriate dilutions of the Mab are added to the cells in a volume of 20 µl/well, and incubated for 1 hr. at 37° C. Each dilution is tested in duplicate wells. PBL are added at a volume of 100 µl/well ($10^5$ cell/well). The final ratio of PBL to K562 cells is ~13:1. PHA (10×) (Sigma L-9132) is added at 20 µl/well (final concentration 0.75 µg/ml). The total volume per well is completed to 200 µl with RPMI/10% FCS. Plates are incubated at 37° C. in a 5% $CO_2$-humidified incubator for 24 hrs. After centrifugation of the plates, the supernatants are collected and IL-2 tested by ELISA (BD, San Diego, Calif., Cat No2627KI), according to the manufacturer' specifications (FIG. 4). To calculate the $IC_{50}$ (Mab concentration that blocks 50% of IL-2 release by OX40L-stimulated PBL), the background IL-2 concentration produced in the control cultures (PBL+PHA+K562WT) was substracted from the total IL-2 produced by PBL-stimulated with K562×OX40L+ cells (FIG. 5). $IC_{50}$ TAG34: 0.07 µM; LC.001: 2 nM; LC.005: 10 nM. The $IC_{50}$ values are in the range between 2 and 10 nM.

Example 17

Tetanus Assay ('TT-Assay') Testing the Inhibitory Effect of Antibodies on Peripheral Blood Lymphocytes Stimulated by Tetanus Toxoid Peripheral blood mononuclear cells (PBMC) were isolated from heparinized blood by Ficoll Hypaque. In most cases freshly isolated PBMC were used for this assay. In some cases also cryopreserved PBMC were used. The medium for this assay was RPMI containing 10% human male AB serum (Sigma-Aldrich); 2 mM Glutamine and Pen/Strep (ready-to-use mixture of antibiotic penicillin and streptomycin (Roche Diagnostics GmbH DE); lyophilisate reconstituted in 20 ml; use of 2 ml per 1000 ml medium).

In order to get adhered to the plastic 300.000 PBMC per well were preincubated overnight in 96 well flat bottom plates.

The next day tetanustoxoid (TT) (Chiron Behring) was added to the wells in a final concentration of 2 to 5 µg/ml. The positive control wells (maximum proliferation/stimulation) only contained TT, to all other wells antibodies (as purified IgG) were added in a final concentration of 10 µg/ml. Murine Mab TAG-34 was included in the assay (final concentration 10 µg/ml). As nonstimulatory background control medium alone was used. All assays were set up in triplicates.

Figure 6:
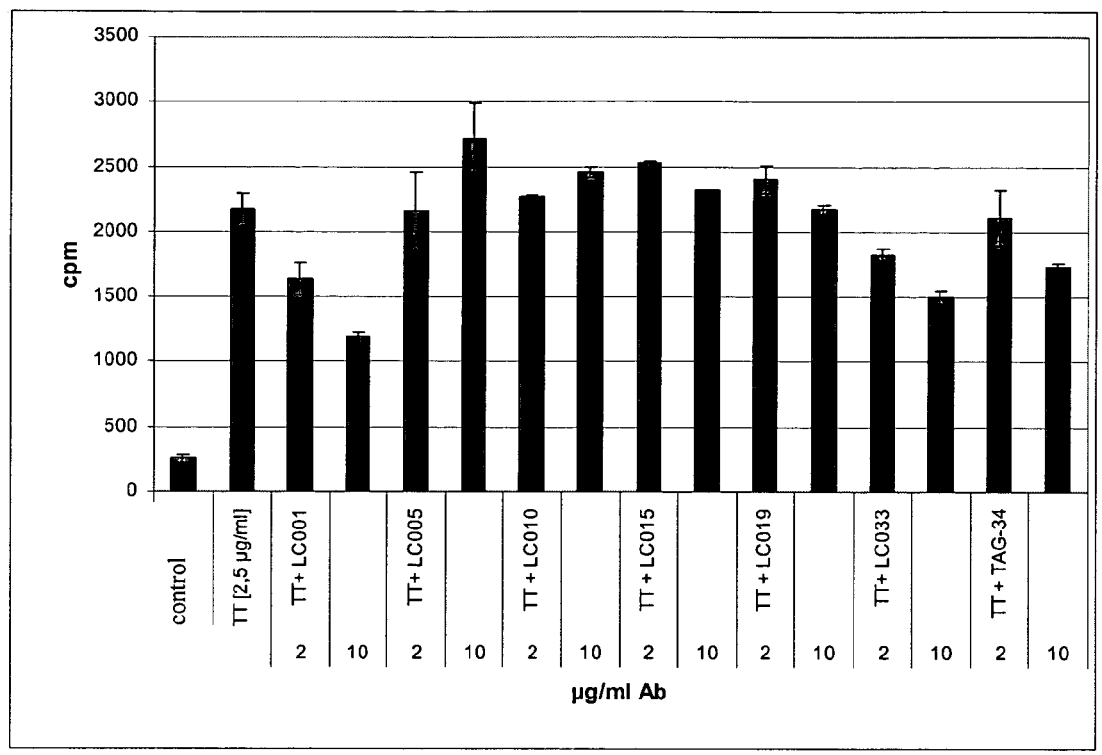
FIG. 6 shows "TT-assay" data for TAG-34, LC.001 and LC.033.

After six days of further incubation (37° C., 5% $CO_2$, 95% humidity) $^3$H-thymidine was added in a final concentration of 1 µCurie/ml and after an additional incubation period of 16 h the plates were harvested and incorporated $^3$H-thymidine was determined in a beta-counter (FIG. 6).

Example 18

Cross-Reactivity of the OX40L Antibodies with Mouse OX40L

To determine the ability of the antibodies of the invention to cross-react with murine OX40L, serial diluted antibody and control antibodies were incubated with K562-mOX40L cells, stably expressing mOX40L. Binding to K562 WT cells and K562-hOX40L cells, stably expressing hOX40L, was also assessed. As negative control a HuMab antibody directed against Keyhole Limpet Hemo-cyanin (alpha-KLH) was used. Antibody R134L, rat anti-mOX40L (eBioscience, San Diego, Calif.) was included as positive control for mOX40L expression. Antibody TAG-34, mouse anti-hOX40L (MBL, Nagoya, Japan) was included as positive control for hOX40L expression. For detection of bound human antibodies, a fluorescein (FITC)-conjugated goat anti-human IgG antibody was used. For the detection of bound RM134L a biotinylated rabbit anti-rat IgG antibody (DAKO, Glostrup, Denmark) was used in combination with streptavidin, conjugated with phycoerythrin (PE) (DAKO). For detection of bound TAG-34, FITC-conjugated rabbit anti-mouse IgG antibody was used. Calculations concerning $EC_{50}$ values or maximum binding at 20 µg/ml (Bmax) of the HuMabs tested were determined using non-linear regression (sigmoidal dose-response with variable slope) using Graphpad Prism software.

Figure 7:
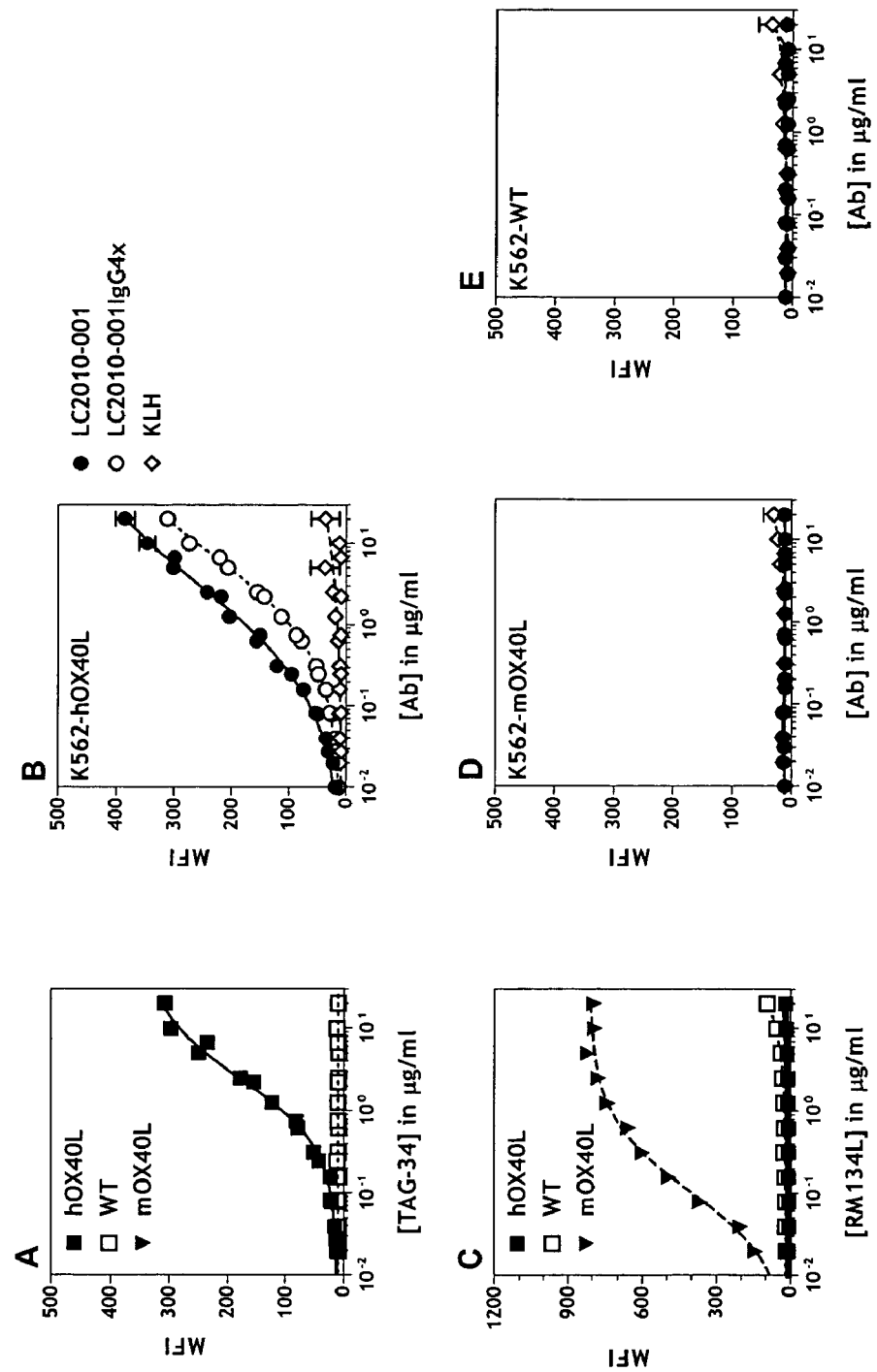
FIG. 7 shows the cross-reactivity of the antibodies of the invention with mouse OX40L. A) control for hOX40L expression on transfected and WT cells, B) binding of the antibodies to hOX40L expressing K562 cells, C) control for mOX40L expression on transfected and WT cells, D) binding of the antibodies to mOX40L expressing K562 cells, and E) binding of the antibodies to WT K562 cells (n=3).

Results: LC.001 according to the invention was able to bind to hOX40L as indicated by an $EC_{50}$ value of 5.16±2.93 µg/ml and a Bmax (MFI) value of 385.22, but not to mOX40L or WT cells as shown by Bmax (MFI) values of 11.41 and 9.67, respectively. Furthermore, LC.001 (IgG4) according to the invention was also able to efficiently bind to hOX40L as indicated by an $EC_{50}$ value of 8.19±1.05 µg/ml and a Bmax (MFI) value of 311.30, but not to mOX40L or WT cells as shown by a Bmax (MFI) value of 13.47 and 9.58, respectively. As expected, the negative control alpha-KLH did not bind to any cells. (FIG. 7). Therefore OX40L antibodies according to the invention show at least 30 fold lower binding to mouse OX40L compared to human OX40L.

Example 19

Potential of OX40L HuMabs to Activate the Complement System

C1q and C3c Binding ELISA: To determine the ability of the antibodies of the invention to induce C1q binding and C3 activation, an ELISA plate was coated with serial diluted antibody and control antibodies. As negative control a human IgG4 (The Binding Site, Birmingham, England), that binds C1q very weakly, was used. Human IgG1 (The Binding Site) and alpha-KLH (IgG1) were included as positive controls. Subsequently, coated antibodies were incubated with recombinant C1q or human pooled serum, as a source of C3. For the detection of bound C1q, a rabbit antibody directed against C1q (DAKO) in combination with a swine anti-rabbit IgG antibody, conjugated with horseradish peroxidase (HRP) (DAKO) were used. For the detection of activated C3c (generated via activation of C3), a mouse anti-human C3c antibody (DAKO) in combination with a rabbit anti-mouse IgG antibody, conjugated with HRP (Jackson ImmunoResearch Laboratories, West Grove, Pa.) were used. To assess differences in coating efficiencies, coated antibodies were visualized with a goat anti-human IgG antibody, conjugated with HRP. Calculations concerning $EC_{50}$ values or maximum binding at 10 µg/ml (Bmax) of the HuMabs tested were determined using non-linear regression (sigmoidal dose-response with variable slope) using Graphpad Prism software.

Results: LC.001 according to the invention was able to bind C1q efficiently as indicated by an $EC_{50}$ value of 2.19±0.42 µg/ml and a Bmax ($OD_{405}$) value of 3.089. Furthermore, both positive control human IgG1 and anti-KLH could bind C1q efficiently, as indicated by EC50 values of 4.17±1.08 µg/ml and 2.57±1.51 µg/ml respectively, and Bmax ($OD_{405}$) values of 2.685 and 3.306 respectively. As expected, the negative control human IgG4 did not bind C1q, as shown by an $OD_{405}$ Bmax value of 0.353. Moreover, LC.001gG4x according to the invention had lost the capacity to bind C1q, as shown by an $OD_{405}$ Bmax value of 0.357.

Figure 8:
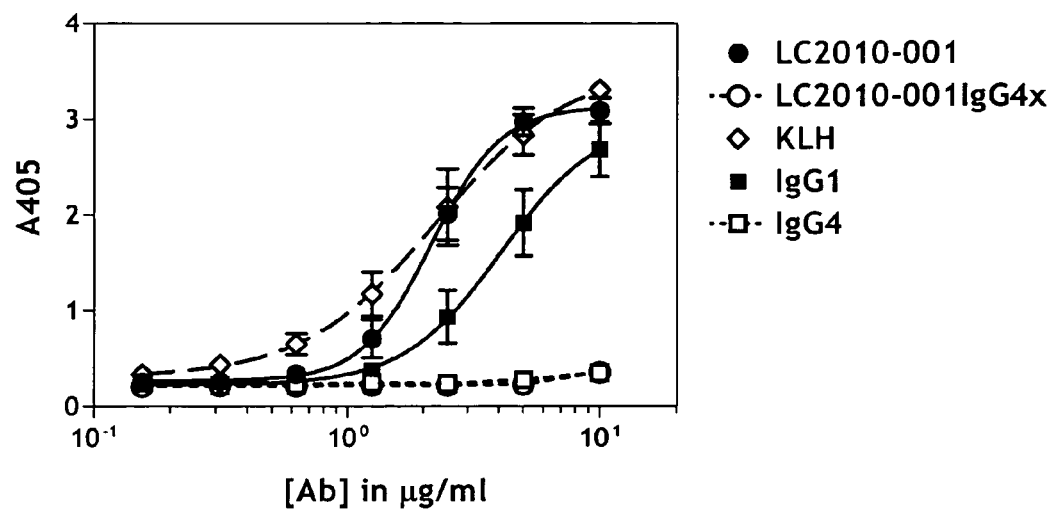
FIG. 8 shows the ability of the antibodies of the invention to bind C1q (n=3).
Figure 9:
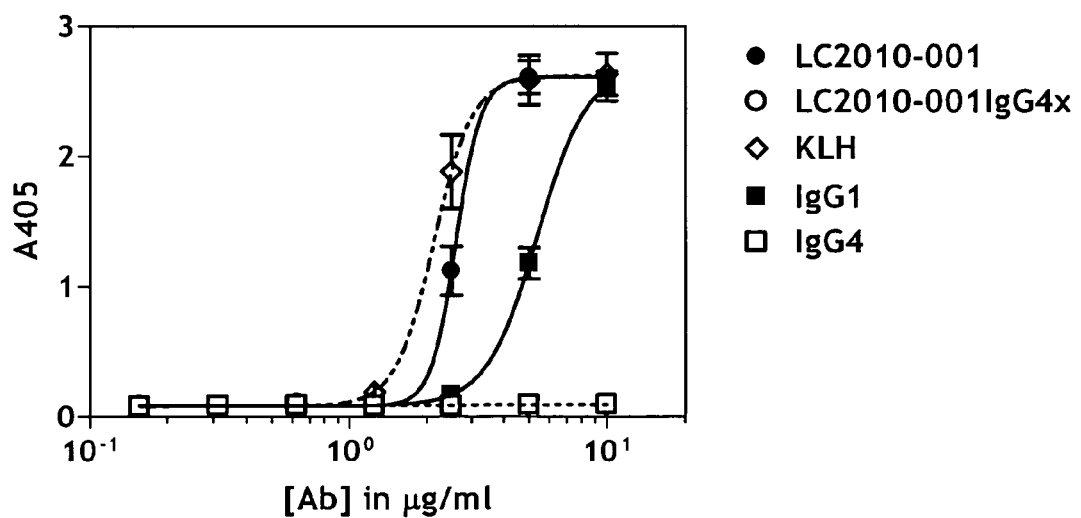
FIG. 9 shows the ability of the antibodies of the invention to activate C3c (n=3).

In line with the C1q binding capacities, C3c deposition by LC.001 occurred in an antibody-concentration dependent manner, with an EC50 value of 2.67±0.16 µg/ml and a Bmax ($OD_{405}$) value of 2.614. Furthermore, both positive controls human IgG1 and anti-KLH could deposit C3c efficiently, as indicated by $EC_{50}$ values of 5.45±0.36 µg/ml and 2.16±0.26 µg/ml respectively, and Bmax ($OD_{405}$) values of 2.543 and 2.633,respectively. As expected, the negative control human IgG4 did not deposit C3c, as shown by an $OD_{405}$ Bmax value of 0.095. Moreover, LC.001 IgG4x according to the invention had lost the capacity to deposit C3c, as shown by an $OD_{405}$ Bmax value of 0.090. (FIGS. 8 and 9).

Example 20

Potential of OX40L HuMabs to Bind to Fcγ Receptors I, Ia and IIb

IgG-induced antibody-dependent cellular cytotoxicity (ADCC) is mediated by Fcγ receptors (FcγR) on effector cells. To determine the ability of the antibodies of the invention to bind to FcγR5, IIA1.6 cells (derived by limited dilution from IIA1 cells; Jones, B., et al., *J. Immunol.* 136 (1986) 348-356) stably transfected with human FcγRI, FcγRIIa, FcγRIIb and wild-type cells were incubated with serial diluted antibody and control antibodies. As negative controls, human IgG2 (The Binding Site Ltd., UK), that does not bind FcγRI, and human IgG4 (The Binding Site), that does not bind FcγRII, were used. Human IgG1 (The Binding Site) was included as positive control for FcγRI binding and human IgG3 (The Binding Site) for FcγRII binding. Bound antibodies were detected by FACS analysis using an antibody directed against human IgG conjugated with phycoerythrin (PE). Calculations concerning $EC_{50}$ values or maximum binding at 10 µg/ml (Bmax) of the HuMab tested were determined using nonlinear regression curve fitting (variable slope) using Graphpad Prism software.

LC.001 was able to bind to FcγRI efficiently (comparable to the control IgG1 antibody) as indicated by an $EC_{50}$ value of 0.11±0.03 μg/ml and a Bmax (MFI) value of 8041.54, but not to FcγRIIa and FcγRIIb as shown by Bmax (MFI) values of 25.06 and 21.18, respectively.

Figure 10:
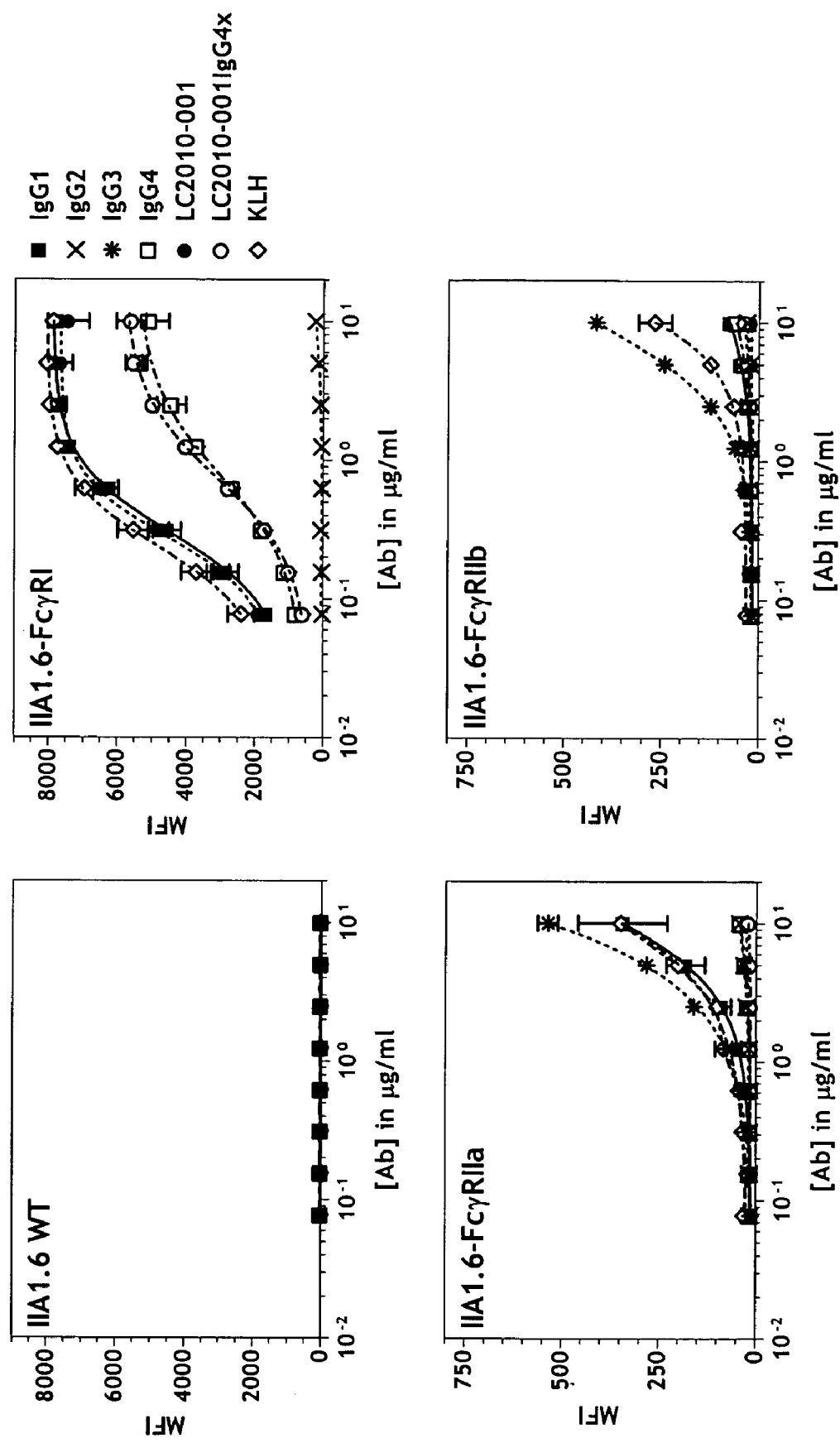
FIG. 10 shows the ability of the antibodies of the invention to bind to FcγRI (n=4), FcγRIIa (n=4) and FcγRIIb (n=4).
Figure 11:
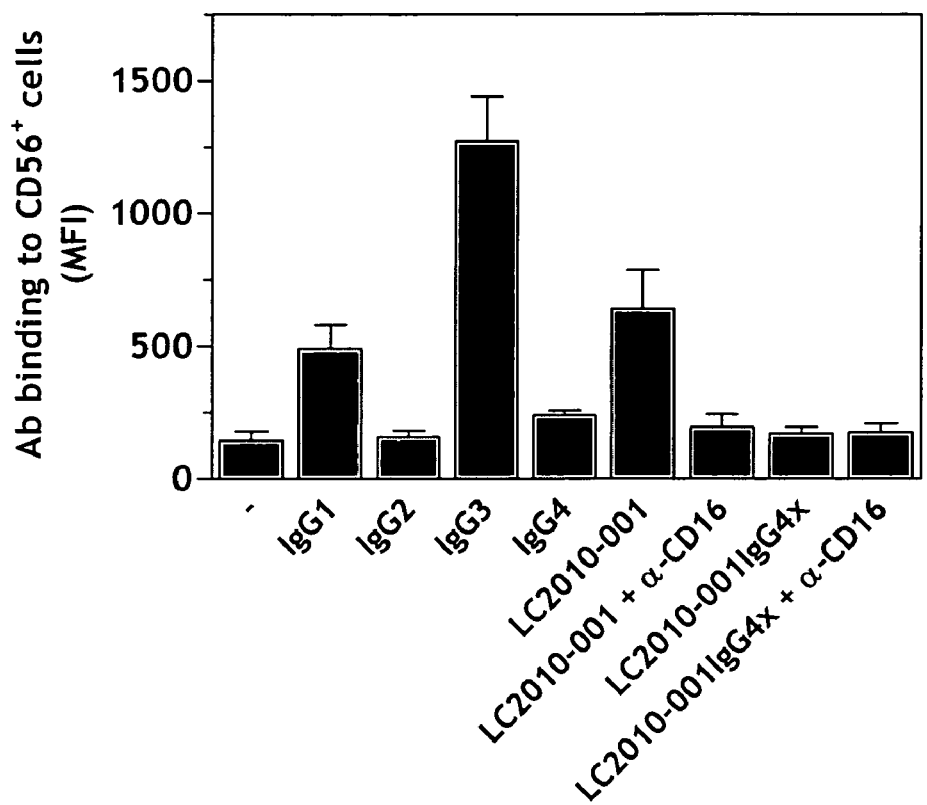
FIG. 11 shows the ability of the antibodies of the invention to bind to FcγRIIIa (CD16) on NK cells (Mean±SEM of 6 donors).

LC.001IgG4x was less efficient in binding to FcγRI compared to LC.001 and was comparable to the control IgG4 antibody, with an $EC_{50}$ value of 0.86±0.12 μg/ml and a Bmax (MFI) value of 6030.07. No binding of LC.001 IgG4x to FcγRIIa and FcγRIIb was observed (Bmax (MFI) values of 21.40 and 19.27, respectively), whereas control IgG3 antibody was able to bind (Bmax (MFI) values of 536.65 and 418.59, respectively) (FIG. 10). The $EC_{50}$ value for binding to FcγRI is therefore for LC.001IgG4x eight fold compared to the $EC_{50}$ value of antibody LC.001.

Example 21

Potential of OX40L HuMabs to Bind to FcγRIIIa on NK Cells

To determine the ability of the antibodies of the invention to bind to FcγRIIIa (CD16) on Natural Killer (NK) cells, Peripheral Blood Mononuclear Cells (PBMCs) were isolated and incubated with 20 μg/ml of HuMab antibody and control antibodies in the presence or absence of 20 μg/ml of a blocking mouse antibody to FcγRIIIa (anti-CD16, clone 3G8, RDI, Flanders, N.J.), to verify binding via FcγRIIIa. As negative controls, human IgG2 and IgG4 (The Binding Site), that do not bind FcγRIIIa, were used. Human IgG1 and IgG3 (The Binding Site) were included as positive controls for FcγRIIIa binding. Bound antibodies on NK cells were detected by FACS analysis using a PE-labeled mouse anti-human CD56 (NK-cell surface marker) antibody (BD Biosciences Pharmingen, San Diego, Calif.) in combination with a FITC-labeled goat F(ab)₂ anti-human IgG (Fc) antibody (Protos immunoresearch, Burlingame, Calif.). Maximum binding at 20 μg/ml (Bmax) of the HuMab tested was determined.

LC.001 was able to bind to FcγRIIIa efficiently (comparable to the control IgG1 antibody) as indicated by a Bmax (MFI) value of 641.37. Addition of a blocking antibody against FcγRIIIa abolished binding of LC.001 to NK cells (Bmax (MFI) value of 194.61 compared to background staining of 145.38). LC.001 IgG4x did not bind to FcγRIIIa and behaved comparable to the control IgG4 antibody, with a Bmax (MFI) value of 170.52, resulting in a Bmax of LC.001 IgG4x which is about only 10% of Bmax of LC.001. Addition of a blocking antibody against FcγRIIIa had no effect on LC.001 IgG4x binding (Bmax (MFI) value of 174.26) (FIG. II).

Example 22

Effect of hMab_hOX40L and Mab TAG-34 Binding to HUVEC (Primary Human Umbilical Vein Endothelial Cells/PromoCell)

Endothelial cells were described to express hOX40L (Kotani, A., et al., *Immunol. Lett.* 84 (2002) 1-7). Human umbilical vein endothelial cells (HUVEC) naturally express hOX40L and therefore could be used as "endothelial cell model". Aim of this assay was to determine the fate of hOX40L on HUVEC cells after binding to antibodies TAG-34 and LC.001.

HUVEC were thawed and expanded in ECG-M media plus 2% FCS for 4 days. in T175-flasks (Sarstedt). The cells were plated into 24-well plates (10.000 cells/well).

After 3 days the media was changed to ECG-M+0.5% FCS. Addition of antibody (<KLH>(antibody against Keyhole Limpet Hemocyanin), TAG-34 or LC.001 for induction of down-modulation) at 10 μg/ml and incubation for 2,5 h or 24 h. Restaining of the HUVEC cells with TAG-34 or LC.001. FACS-staining with secondary antibody against murine IgG, labelled with Alexa488 (=<m>) or against human IgG, labelled with Alexa488 (=<h>) each 10 μg/ml. FACS-measurement was done in FACS-scan (Becton Dickinson) and mean fluorescence intensity (MFI) was calculated.

The <KLH> antibody was used as unspecific, negative control. Table 7 shows that addition of LC.001 does not result in down-modulation of OX40L expression on HUVEC cells neither after 2.5 nor after 24 h (compare line 4 with line 5 and 6). However addition of TAG 34 shows a strong (about 3-fold) down-modulation of hOX40L on HUVEC cells after 2.5 h as well as after 24 h (compare line 10 with line II and 12).

Antibodies according to the invention in a concentration of 10 μg/ml do not induce downregulation of OX40L expression on HUVEC cells.

TABLE 7

| | | | MFI | |
|---|---|---|---|---|
| Mab used for downmodulation | Mab used for staining | secondary Mab for FACS | 2.5 h | 24 h |
| 1. media control | — | <h> | 5.17 | 5.39 |
| 2. media control | LC.001 | <h> | 28.52 | 24.99 |
| 3. <KLH> | — | <h> | 4.76 | 4.74 |
| 4. <KLH> | LC.001 | <h> | 31.44 | 23.07 |
| 5. LC.001 | — | <h> | 36.52 | 30.78 |
| 6. LC.001 | LC.001 | <h> | 38.58 | 38.69 |
| 7. media-control | — | <m> | 3.66 | 3.18 |
| 8. media-control | TAG-34 | <m> | 31.81 | 25.32 |
| 9. <KLH> | — | <m> | 3.68 | 3.43 |
| 10. <KLH> | TAG-34 | <m> | 30.79 | 31.58 |
| 11. TAG-34 | — | <m> | 9.44 | 7.39 |
| 12. TAG34 | TAG-34 | <m> | 8.97 | 14.89 |

Example 23

Western Blot Analysis of TAG34, LC.001 and LC.005

40 and 100 ng hOx40L-His (R&D Systems, with a theoretical size of 28-34 kDa) and the molecular weight marker Magik Mark XP (Invitrogen; 20, 30, 40, 50, 60, 80, 100, 120, 220 kDa) were prepared for gel-electrophoresis. Therefore x μl Protein, 2.5 μl NuPage LDS (lithium salt of dodecyl sulfate)

Sample Buffer (4×), 1 μl NuPage Reducing Agent (10×), and H₂O and 10 μl were put together and denatured for 10 min. at 70° C. After that the samples were loaded onto a NuPage gel (Novex; 10% Bis-Tris) and run for 1 h at 150V in 1×MOPS Running Buffer (Novex).

The gel was blotted by a Semi-Dry-Blot onto a PVDF Membrane (Millipore; activation of the membrane by 5 min. incubation in methanol and 10 min incubation in 1× transfer buffer) using 1× NuPage Transfer Buffer (Ix buffer, 0.1% Antioxidance, 10% methanol) for 1 h/50 mA in a semi dry chamber. The membrane was blocked in 1×PBS/5% milk/0.5% Tween under shaking for 1 h at RT. The primary antibody (pAB) was diluted in 1×PBS/1% milk/0.5% Tween, added and incubated overnight at 4° C.

| | |
|---|---|
| LC.001: | 1.9 µl (1.6 µg) in a total volume of 4 ml |
| LC.005: | 1.1 µl (1.6 µg)/4 ml |
| TAG34: | 1.6 µl (1.6 µg)/4 ml |

Figure 12:
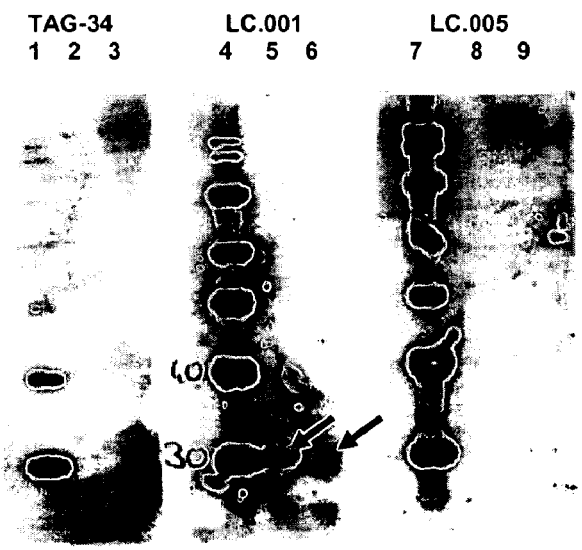
FIG. 12 Western Blot; lanes 1, 4, 7: marker; lanes 2, 5, 8: 100 ng OX40L; lanes 3, 6, 9: 40 ng OX40L.

The membrane was washed 3× for 10 min in 1×PBS/0.5% Tween. The secondary antibody (sAB) was diluted in 1×PBS/1% milk/0.5% Tween, added and incubated for 1.5 h at RT. For LC.001 and LC.005 polyclonal antibody against human IgG (Pierce) in a 1:10000 dilution was used as sAB; for TAG34 polyclonal antibody against mouse IgG from the Lumi-Light Western Blotting Kit (Roche) in a 1:400 dilution was used as sAB. The membrane was washed 2× for 30 min with 1×PBS/0.5% Tween. For detection the Lumi-Light Western Blotting Kit (Roche) according manufacturer's instruction was used. The results from the western blot were shown in FIG. 12. LC.001 is able to detect (dodecyl sulfate) denatured OX40L whereas LC.005 and TAG34 do not bind to denatured OX40L.

REFERENCES

Akiba, H., et al., *Biochem. Biophys. Res. Commun.* 251 (1998) 131-136
Akiba, H., et al., *J. Exp. Med.* 191 (2000) 375-380
Angal, S., et al., *Mol. Immunol.* 30 (1993) 105-108
Aplin, J. D., and Wriston, J. C. Jr., *CRC Crit. Rev. Biochem.* 10 (1981) 259-306
Arestides, R. S., et al., *Eur. J Immunol.* 32 (2002) 2874-2880
Armour, K. L., et al. *Eur. J. Immunol.* 29 (1999) 2613-2624
Ausubel, F., et al., ed., Current Protocols in Molecular Biology, Greene Publishing and Wiley Interscience, New York (1987)
Barnes, L. M., et al., *Biotech. Bioeng.* 73 (2001) 261-270
Barnes, L. M., et al., *Cytotechnology* 32 (2000) 109-123
Baum, P. R., et al., *EMBO J.* 13 (1994) 3992-4001
Blazar, B. R., et al., *Blood* 101 (2003) 3741-3748
Boerner, P., et al., *J. Immunol.* 147 (1991) 86-95
Bruggemann, M., et al., *Year Immunol.* 7 (1993) 33-40
Brunhouse, R., and Cebra, J. J., *Mol. Immunol.* 16 (1979) 907-917
Burgess, J. K., et al., *J. Allergy Clin. Immunol.* 113 (2004) 683-689
Burton, D. R., et al., *Nature* 288 (1980) 338-344
Burton, D. R., *Mol. Immunol.* 22 (1985) 161-206
Capel, P. J., et al., *Immunomethods* 4 (1994) 25-34
Carter, P., et al., *Proc. Natl. Acad. Sci. USA* 89 (1992) 4285-4289
Chen, J., et al., *EMBO J.* 12 (1993) 821-830
Chen, J., et al., *Int. Immunol.* 5 (1993) 647-656
Choi, T. K., et al., *Nat. Genet.* 4 (1993) 117-123
Cole et al., *Monoclonal Antibodies and Cancer Therapy*, Alan R. Liss, p. 77 (1985)
de Haas, M., et al., *J Lab. Clin. Med.* 126 (1995) 330-341
Duncan, A. R., and Winter, G., *Nature* 332 (1988) 738-740
Durocher, Y., et al., *Nucl. Acids. Res.* 30 (2002) E9
Edelman, G. M., et al., *Proc. Natl. Acad. Sci. USA* 63 (1969) 78-85
Edge, A. S., et al., *Anal. Biochem.* 118 (1981) 131-137
EP 0 307 434
Fishwild, D. M., et al., *Nat. Biotechnol.* 14 (1996) 845-851
Geisse, S., et al., *Protein Expr. Purif.* 8 (1996) 271-282
Gessner, J. E., et al., *Ann. Hematol.* 76 (1998) 231-248
Harding, F., and Lonberg, N., *Ann. N. Acad. Sci.* 764 (1995) 536-546
Hezareh, M., et al., *J. Virol.* 75 (2001) 12161-12168
Higgins, L. M., et al., *J. Immunol.* 162 (1999) 486-493
Hoogenboom, H. R., and Winter, G., *J. Mol. Biol.* 227 (1992) 381-388
Hoshino, A., et al., *Eur. J. Immunol.* 33 (2003) 861-869
Humphreys, I. R., et al., *J. Exp. Med.* 198 (2003) 1237-1242
Idusogie, E. E., et al., *J. Immunol.* 164 (2000) 4178-4184
Imura, A., et al., *Blood* 89 (1997) 2951-2958
Imura, A., et al., *J. Exp. Med.* 183 (1996) 2185-2195
Ishii, N., et al., *Eur. J. Immunol.* 33 (2003) 2372-2381
Jakobovits, A., et al., *Nature* 362 (1993) 255-258
Jakobovits, A., et al., *Proc. Natl. Acad. Sci. USA* 90 (1993) 2551-2555
Jones, B., et al., *J. Immunol.* 136 (1986) 348-356
Jones, P., et al., *Nature* 321 (1986) 522-525
Kabat, E. A., et al., Sequences of Proteins of Immunological Interest, 5th ed., Public Health Service, National Institutes of Health, Bethesda, Md. (1991)
Kaufman, R. J., *Mol. Biotechnol.* 16 (2000) 151-161
Kjaergaard, J., et al., *J. Immunol.* 167 (2001) 6669-6677
Kotani, A., et al., *Immunol. Lett.* 84 (2002) 1-7
Lane, P., *J. Exp. Med.* 191 (2000) 201-206
Lonberg, N., and Huszar, D., *Intern. Rev. Immunol.* 25 (1995) 65-93
Lonberg, N., et al., *Nature* 368 (1994) 856-859
Lonberg, N., Handbook of Experimental Pharmacology 113 (1994) 49-101
Lukas, T. J., et al., *J. Immunol.* 127 (1981) 2555-2560
Lund, J., et al. *FASEB J.* 9 (1995) 115-119
Makrides, S. C., *Protein Expr. Purif* 17 (1999) 183-202
Mallett, S., and Barclay, A. N., *Immunol. Today* 12 (1991) 220-223
Mallett, S., et al., *EMBO J.* 9 (1990) 1063-1068
Marks, J. D., et al., *J. Mol. Biol.* 222 (1991) 581-597
Matsumura, Y., et al., *J. Immunol.* 163 (1999) 3007-3011
Meissner, P., et al., *Biotechnol. Bioeng.* 75 (2001) 197-203
Miura, S., et al., *Mol. Cell. Biol.* 11 (1991) 1313-1325
Morgan, A., et al., *Immunology* 86 (1995) 319-324
Morrison, S. L., et al., *Proc. Natl. Acad. Sci. USA* 81 (1984) 6851-6855
Ndhlovu, L. C., et al., *J. Immunol.* 167 (2001) 2991-2999
Neuberger, M. S., *EMBO J.* 2 (1983) 1373-1378
Neuberger, M. S., et al., *Nature* 314 (1985) 268-270
Nohara, C., et al., *J. Immunol.* 166 (2001) 2108-2115
Norderhaug, L., et al., *J. Immunol. Methods* 204 (1997) 77-87
Ohshima, Y., et al., *J. Immunol.* 159 (1997) 3838-3848
Orlandi, R., et al., *Proc. Natl. Acad. Sci. USA* 86 (1989) 3833-3837
Picard, D., and Schafffier, W., *Nature* 307 (1984) 80-82
Queen, C., et al., *Proc. Natl. Acad. Sci. USA* 86 (1989) 10029-10033
Ravetch, J. V., and Bolland, S., *Annu. Rev. Immunol.* 19 (2001) 275-290
Ravetch, J. V., and Kinet, J. P., *Annu. Rev. Immunol.* 9 (1991) 457-492
Riechmann, L., et al., *Nature* 332 (1988) 323-327
Rogers, P. R., et al., *Immunity* 15 (2001) 445-455
Salek-Ardakani, S., et al., *J. Exp. Med.* 198 (2003) 315-324
Schlaeger, E.-J., and Christensen, K., *Cytotechnology* 30 (1999) 71-83
Schlaeger, E.-J., *J. Immunol. Methods* 194 (1996) 191-199
Shields, R. L., et al., *J. Biol. Chem.* 276 (2001) 6591-6604
Sojahr, H. T., and Bahl, O. P., *Arch. Biochem. Biophys.* 259 (1987) 52-57
Stüber, E., and Strober, W., *J. Exp. Med.* 183 (1996) 979-989
Stüber, E., et al., *Gastroenterology* 115 (1998) 1205-1215
Sugamura, K., et al., *Nat. Rev. Immunol.* 4 (2004) 420-431

Takahashi, Y., et al., *J. Virol.* 75 (2001) 6748-6757
Takasawa, N., et al., *Jpn. J. Cancer Res.* 92 (2001) 377-382
Tanaka, Y., et al, Int. J. Cancer 36 (1985) 549-555
Taylor, L., and Schwarz, H., *J. Immunol. Meth.* 255 (2001) 67-72
Taylor, L., et al., *Int. Immunol.* 6 (1994) 579-591
Taylor, L., et al., *Nucleic Acids Res.* 20 (1992) 6287-6295
Thommesen, J. E., et al., *Mol. Immunol.* 37 (2000) 995-1004
Thotakura, N. R., and Bahl, O. P., *Meth. Enzymol.* 138 (1987) 350-359
Tozawa, H., et al., *Int. J. Cancer* 41 (1988) 231-238
Tsukada, N., et al., *Blood* 95 (2000) 2434-2439
Tuaillon, N., et al., *J. Immunol.* 152 (1994) 2912-2920
Tuaillon, N., et al., *Proc. Natl. Acad. Sci. USA* 90 (1993) 3720-3724
U.S. Pat. No. 4,179,337
U.S. Pat. No. 4,301,144
U.S. Pat. No. 4,496,689
U.S. Pat. No. 4,640,835
U.S. Pat. No. 4,670,417
U.S. Pat. No. 4,791,192
U.S. Pat. No. 5,202,238
U.S. Pat. No. 5,204,244
U.S. Pat. No. 5,545,806
U.S. Pat. No. 5,545,807
U.S. Pat. No. 5,569,825
U.S. Pat. No. 5,625,126
U.S. Pat. No. 5,633,425
U.S. Pat. No. 5,661,016
U.S. Pat. No. 5,770,429
U.S. Pat. No. 5,789,650
U.S. Pat. No. 5,814,318
U.S. Pat. No. 5,874,299
U.S. Pat. No. 5,877,397
van de Winkel, J. G., and Anderson, C. L., *J. Leukoc. Biol.* 49 (1991) 511-524
van Dijk, M. A., and van de Winkel, J. G., *Curr. Opin. Chem. Biol.* 5 (2001) 368-374
Vitetta, E. S., et al., *Science* 238 (1987) 1098-1104
Ward, E. S., and Ghetie, V., *Ther. Immunol.* 2 (1995) 77-94
Weinberg, A. D., et al., *J. Immunol.* 162 (1999) 1818-1826
Weinberg, A. D., et al., *Nature Medicine* 2 (1996) 183-189
Weinberg, A. D., et al., *Semin. Immunol.* 10 (1998) 471-480
Weinberg, A. D., *Trends Immunol.* 23 (2002) 102-109
Werner, R. G., et al., *Arzneimittelforschung* 48 (1998) 870-880
WO 01/14424
WO 87/05330
WO 92/03918
WO 92/22645
WO 93/1227
WO 94/11026
WO 94/25585
WO 95/12673
WO 95/21915
WO 98/24884
WO 99/15200
Wu, T., et al., *Transplant. Proc.* 33 (2001) 217-218
Yoshioka, T., et al., *Eur. J. Immunol.* 30 (2000) 2815-2823

The invention claimed is:

1. An antibody, characterized in that said antibody binds OX40L, contains a Fc part derived from human origin, the light chain variable domain defined by amino acid sequence SEQ ID NO:11 or 16 and the heavy chain variable domain defined by SEQ ID NO:12, and does not bind complement factor C1q.

2. The antibody according to claim 1, characterized in that the antibody does not bind to human Fcγ receptors on NK cells.

3. The antibody according to claim 2, characterized in that the antibody is a human antibody.

4. The antibody according to claim 2, characterized in that the antibody is a chimeric or humanized antibody.

5. The antibody according to claim 1, wherein the antibody binds to OX40L with a $K_D$ value of less than $10^{-8}$ M.

6. The antibody according to claim 5, wherein the $K_D$ range is between about $10^{-12}$ to about $10^{-9}$ M.

7. The antibody according to claim 6, characterized in that the antibody is an antibody of human subclass IgG1, containing one or more mutations selected from PVA236, GLPSS331 and/or L234A/L235A (numbering according to EU index).

8. The antibody according to claim 6, characterized in that the antibody is an antibody of human subclass IgG4.

9. The antibody according to claim 8, characterized in containing mutation S228P.

10. The antibody according to claim 8, characterized in containing mutation L235E.

11. The antibody according to claim 1, characterized in that does not activate complement factor C3.

12. The antibody according to claim 1, characterized in that it does not elicit complement-dependent cytotoxicity (CDC).

13. The antibody according to claim 1, characterized in that it does not elicit antibody-dependent cellular cytotoxicity (ADCC).

14. The antibody according to claim 1, characterized in that it shows in an ELISA assay inhibition by blocking the interaction of immobilized OX40L with soluble OX40 at a coating concentration of 0.5 μg/ml OX40L, with an IC50 value in the range of 1 nM-4 nM.

15. An antibody, characterized in that said antibody binds OX40L and that the antibody comprises a variable region combination including the light chain variable domain defined by amino acid sequence SEQ ID NO:11 OR 16 and the heavy chain variable domain defined by SEQ ID NO:12.

16. The antibody according to claim 1, characterized in that the human light chain variable region comprises amino acid sequence SEQ ID NO:11.

17. The antibody according to claim 1, characterized in that the human light chain variable region comprises amino acid sequence SEQ ID NO:16.

18. The antibody according to claim 1, characterized in that the antibody comprises at least one amino acid mutation in the Fc part causing non-binding to complement factor C1q.

19. The antibody according to claim 18, characterized in that the antibody comprises a kappa light chain constant region as defined by SEQ ID NO:13.

20. The antibody according to claim 19, characterized in that the antibody comprises a constant region as defined by SEQ ID NO:14 or SEQ ID NO:15.

21. An antibody binding to OX40L, comprising a variable light chain and a variable heavy chain, characterized in that the variable heavy chain comprises CDR1 SEQ ID NO:20, CDR2 SEQ ID NO:25, and CDR3 SEQ ID NO: 29 and/or the variable light chain comprises CDR1 SEQ ID NO:33, CDR2 SEQ ID NO: 38, and CDR3 selected from SEQ ID NOs:43-44.

22. An antibody characterized in that it is produced by the cell line hu-Mab<hOX40L>LC.033.

23. The antibody according to claim 1 characterized in that the antibody is a Fab, F(ab')$_2$ or a single-chain fragment.

24. A composition comprising an antibody molecule of claim 1 or an antibody molecule produced by the method for producing an antibody according to claim 1, wherein said antibody is characterized in that the antibody binds to OX40L, with a $K_D$ value of less than $10^{-8}$ M and is modified in such a manner that said modified antibody does not bind complement factor C1q and/or human Fcγ receptor on NK cells, said method comprising:
   a) providing a host cell comprising an expression vector which comprises a modified first nucleic acid and a second nucleic acid encoding the light chain of said antibody;
   b) culturing said host cell under conditions that allow synthesis of said antibody; and
   c) recovering said antibody from said host cell
or by said method, wherein the sequence of said first nucleic acid encoding the heavy chain of said antibody encodes the heavy chain of an antibody according to claim 22.

25. The composition of claim 24, further comprising a pharmaceutically acceptable excipient.

26. A pharmaceutical composition comprising an antibody of claim 1 and a pharmaceutically acceptable excipient.

* * * * *